United States Patent [19]
Hart

[11] Patent Number: 5,846,251
[45] Date of Patent: Dec. 8, 1998

[54] ACCESS DEVICE WITH EXPANDABLE CONTAINMENT MEMBER

[76] Inventor: Charles C. Hart, 8252 Mandeville, Huntington Beach, Calif. 92646

[21] Appl. No.: 686,175

[22] Filed: Jul. 22, 1996

[51] Int. Cl.[6] .................................................. A61B 17/22
[52] U.S. Cl. ............................................................ 606/127
[58] Field of Search ........................... 600/562; 606/106, 606/114, 127

[56] References Cited

U.S. PATENT DOCUMENTS

| | | | |
|---|---|---|---|
| 4,243,040 | 1/1981 | Beecher | 606/127 |
| 4,271,839 | 6/1981 | Fogarty et al. | 606/127 |
| 4,324,262 | 4/1982 | Hall | 128/756 |
| 4,437,859 | 3/1984 | Whitehouse | 604/131 |
| 4,530,698 | 7/1985 | Goldstein | 604/271 |
| 4,921,478 | 5/1990 | Solano et al. | 604/53 |
| 4,997,435 | 3/1991 | Demeter | 606/127 |
| 5,011,488 | 4/1991 | Ginsburg | 606/159 |
| 5,092,839 | 3/1992 | Kipperman | 604/53 |
| 5,190,561 | 3/1993 | Graber | 606/127 |
| 5,197,968 | 3/1993 | Clement | 606/115 |
| 5,222,970 | 6/1993 | Reeves | 606/195 |
| 5,234,425 | 8/1993 | Fogarty | 606/1 |
| 5,250,038 | 10/1993 | Melker | 604/264 |
| 5,256,146 | 10/1993 | Ensminger | 604/104 |
| 5,281,205 | 1/1994 | McPherson | 604/267 |
| 5,295,969 | 3/1994 | Fischell | 604/168 |

*Primary Examiner*—Max Hindenburg

[57] ABSTRACT

An access device having a single sheath is inserted into a body passage puncture, with an expandable member of the access device held to a minimum diameter. The expandable member is held to the minimum diameter using structure that does not increase the diameter of the access device, rather than a large-diameter external sheath. The structure for holding the expandable member to a minimum diameter can subsequently be removed from the lumen of the access device, once the expandable member has been expanded.

35 Claims, 19 Drawing Sheets

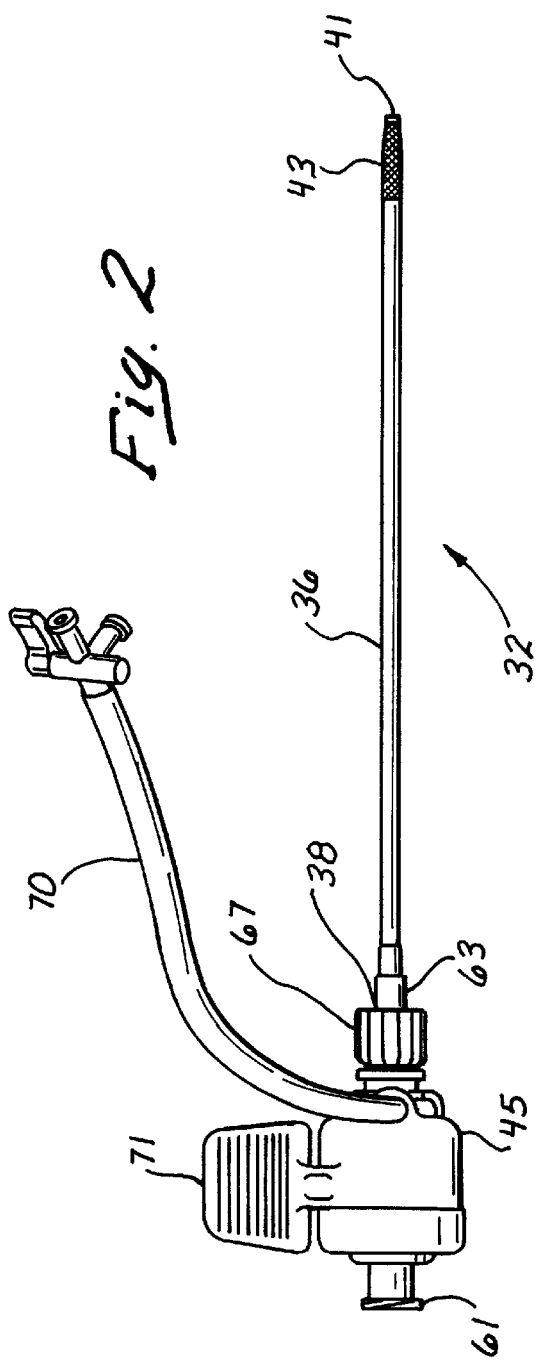
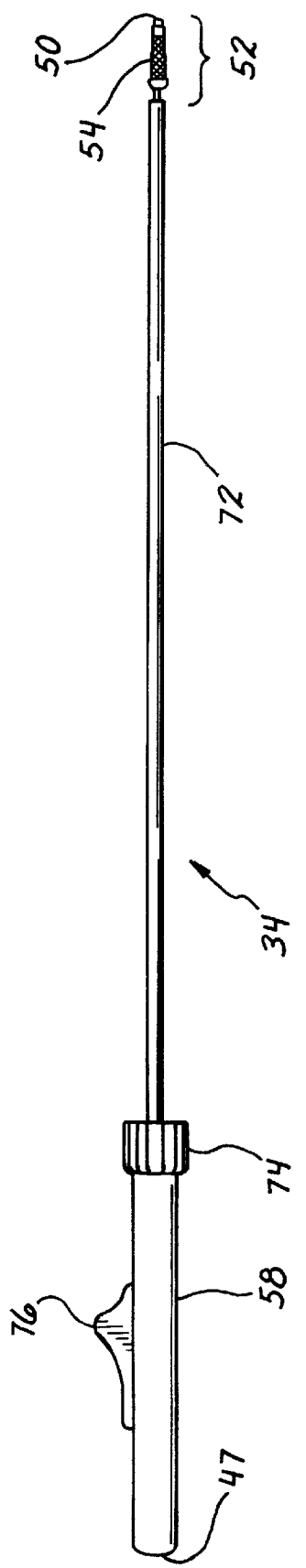

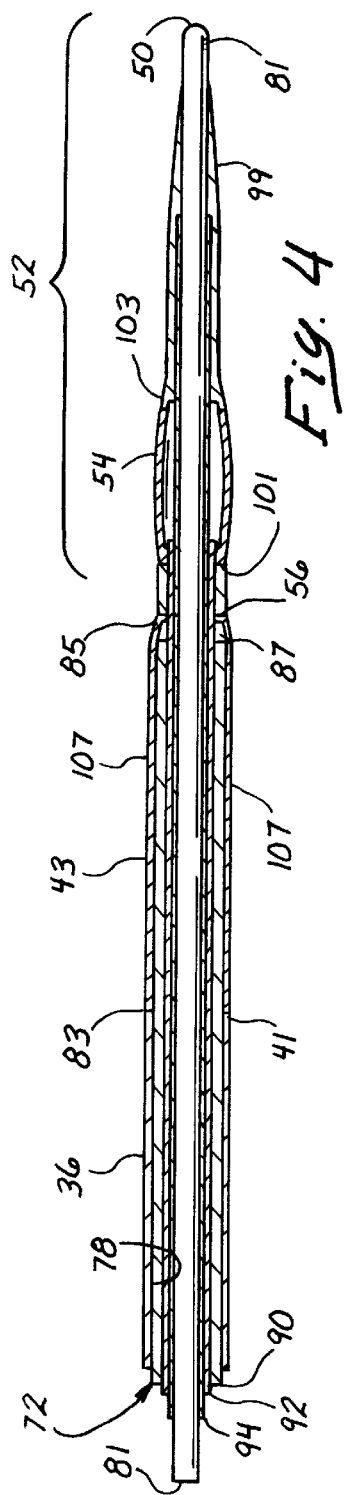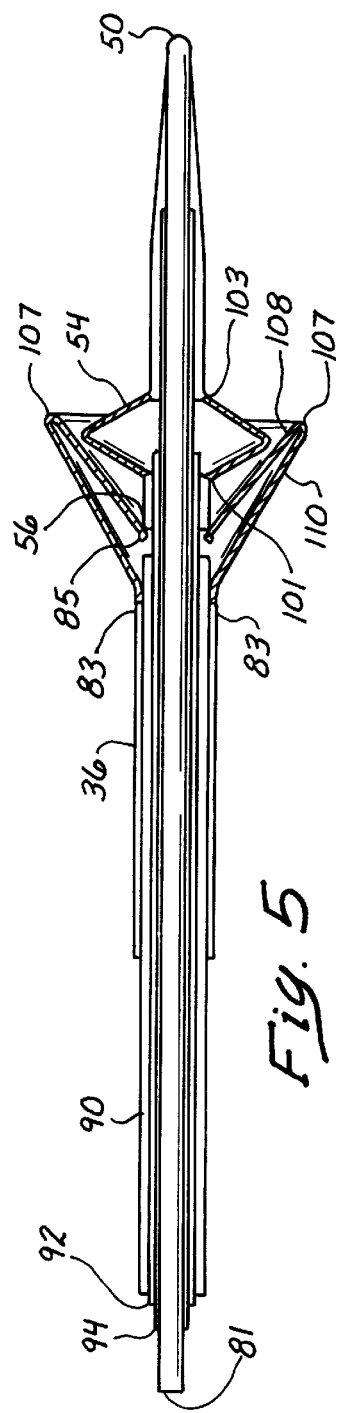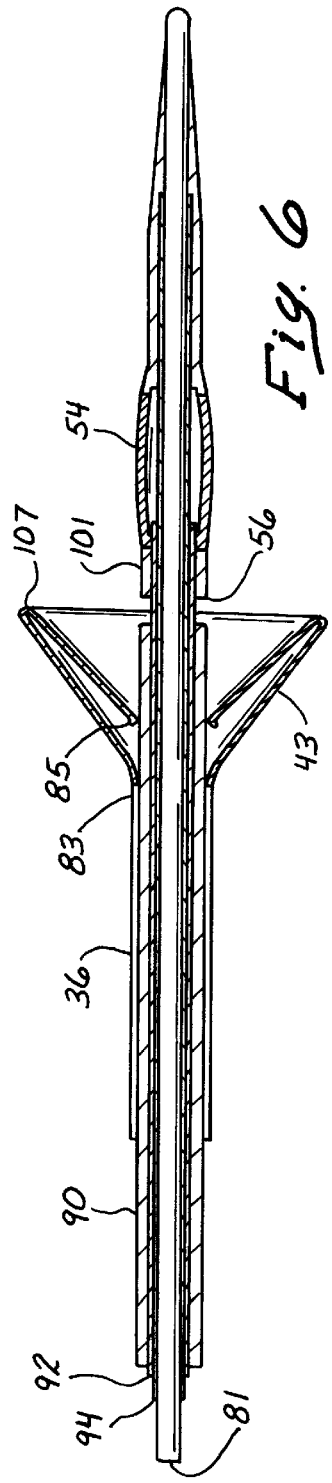

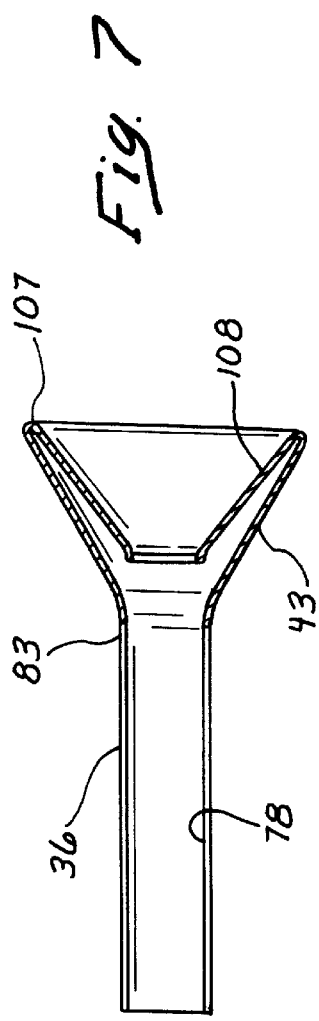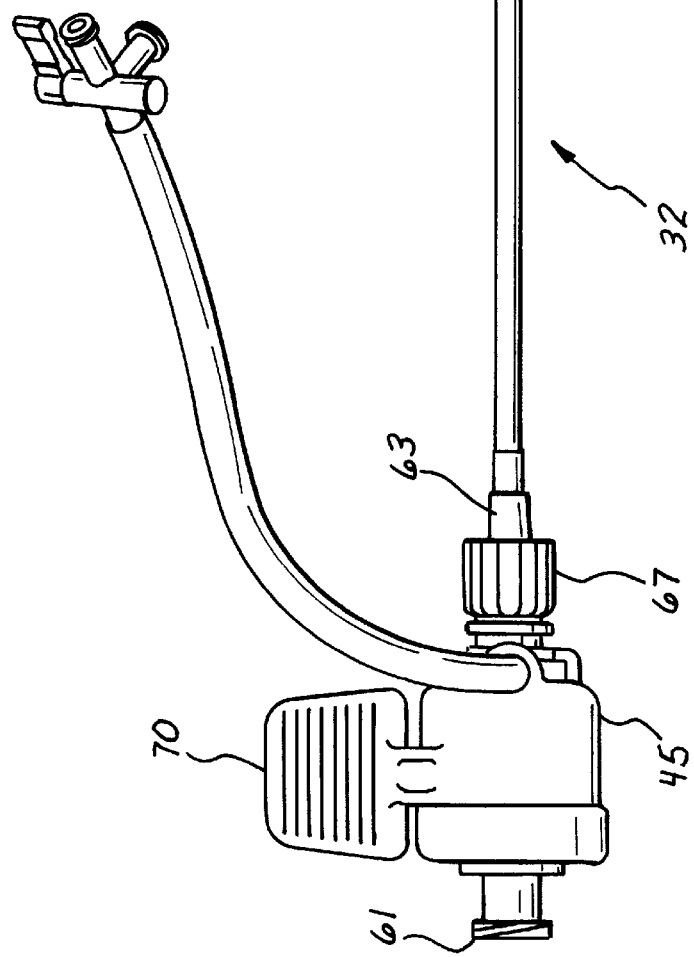

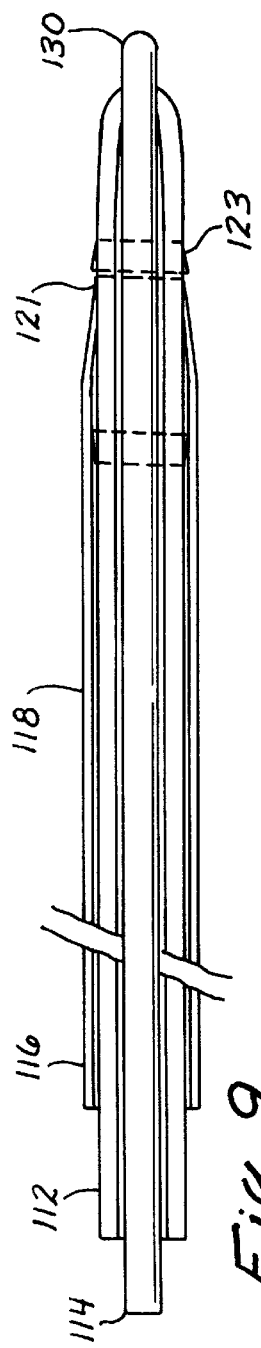
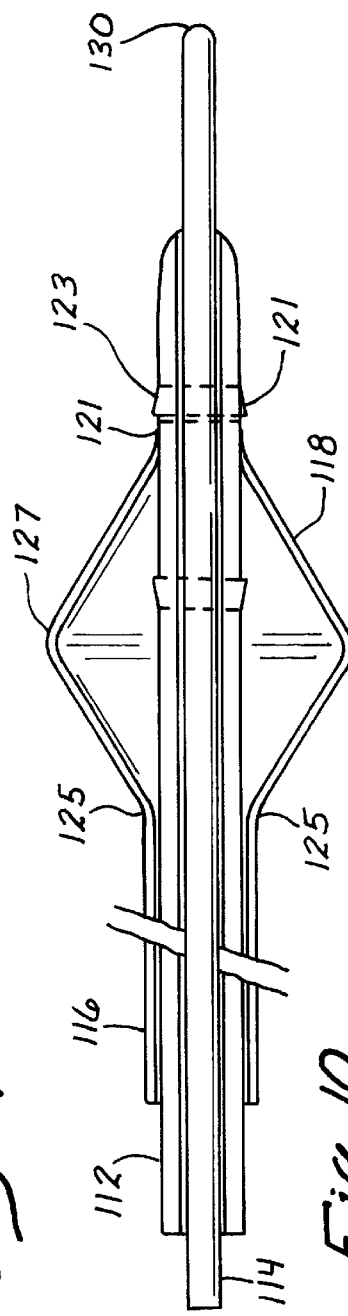
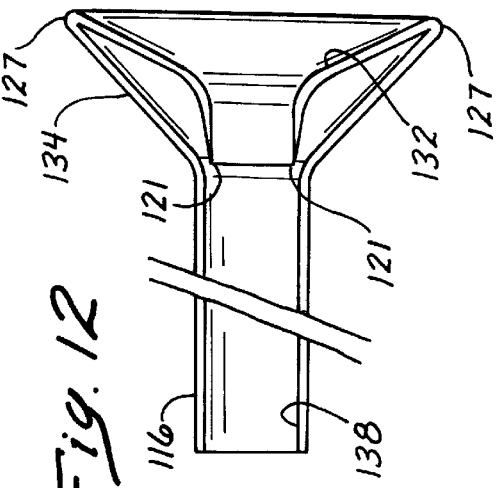
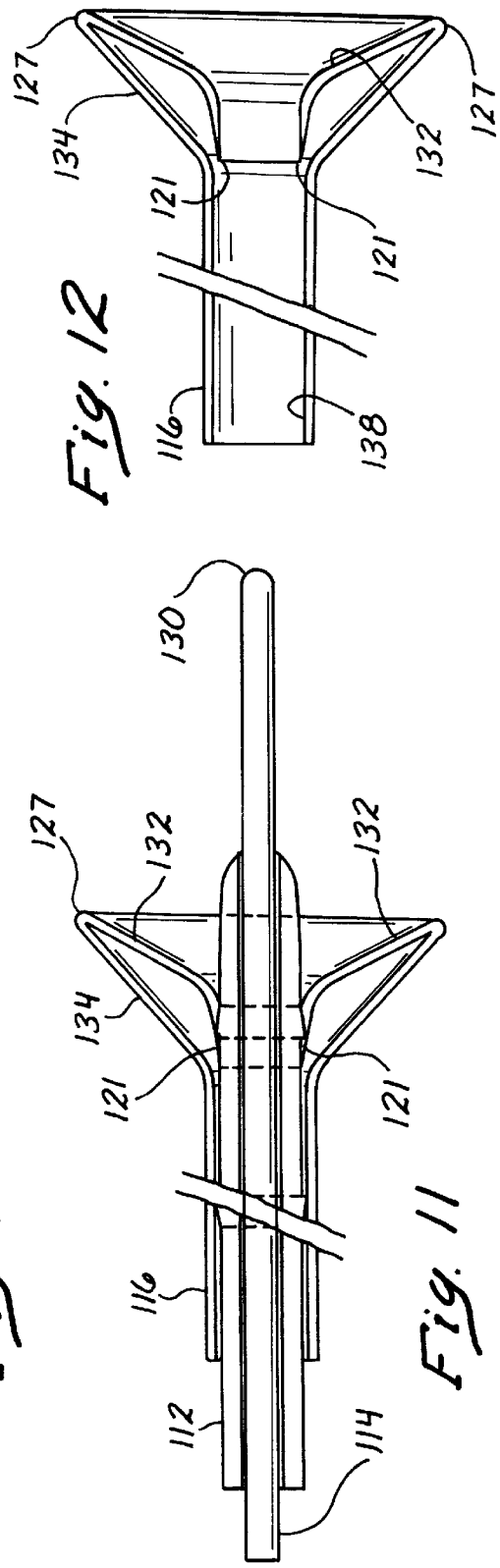

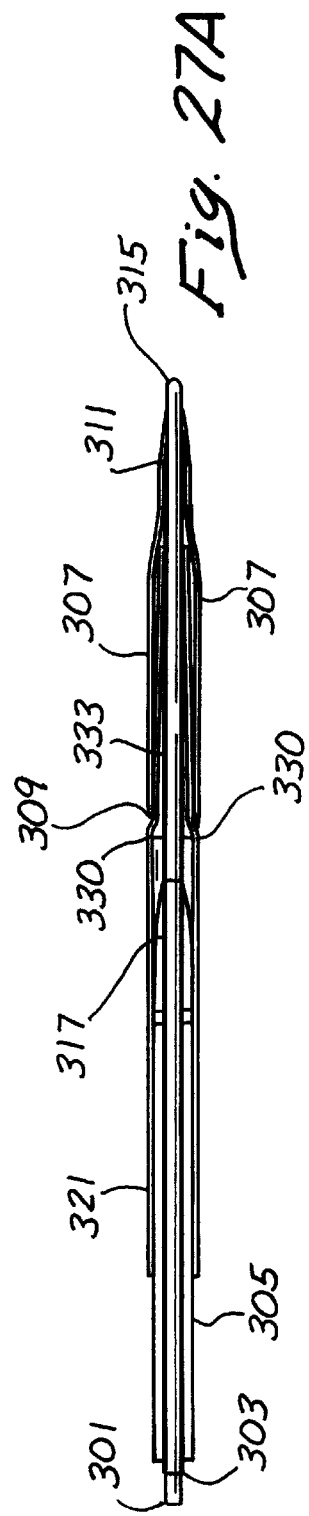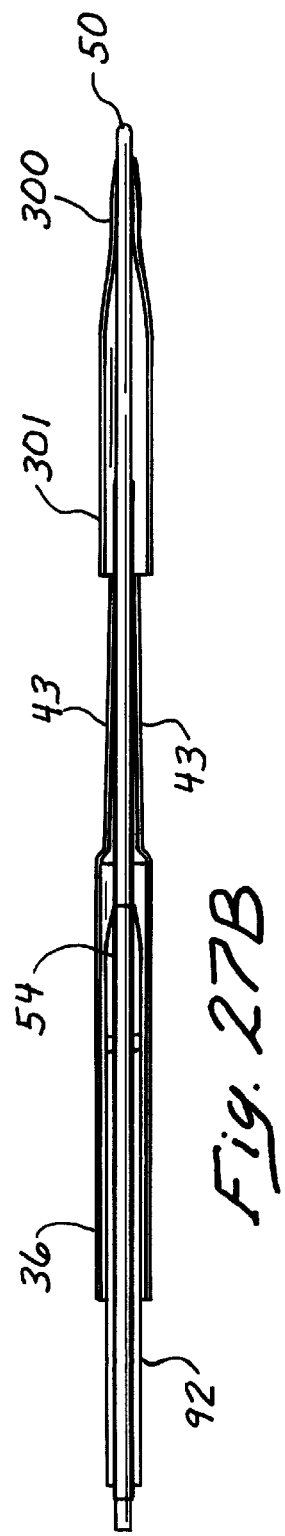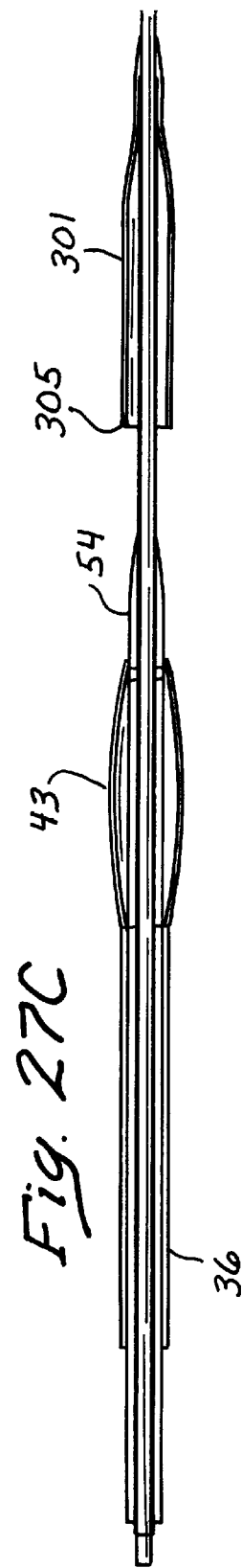

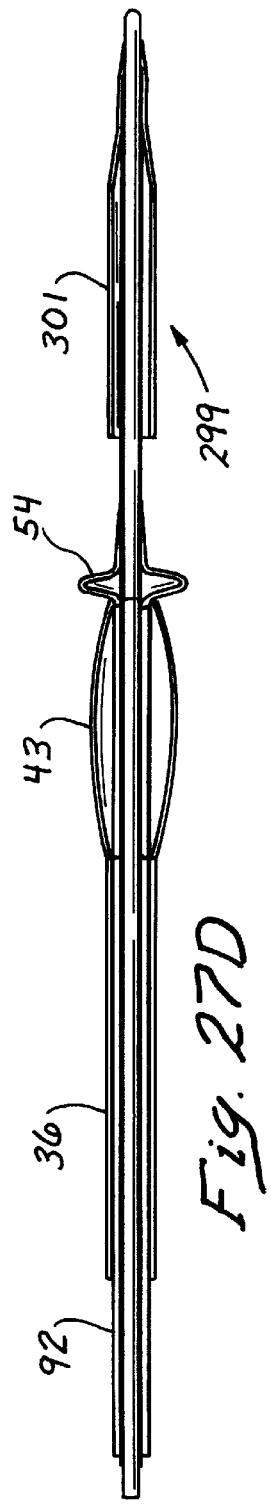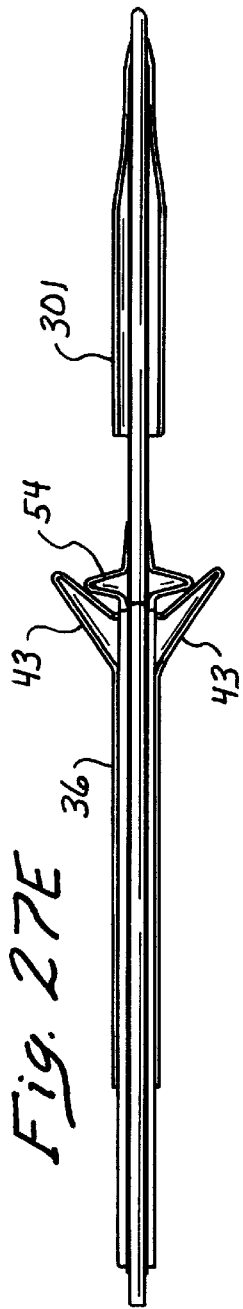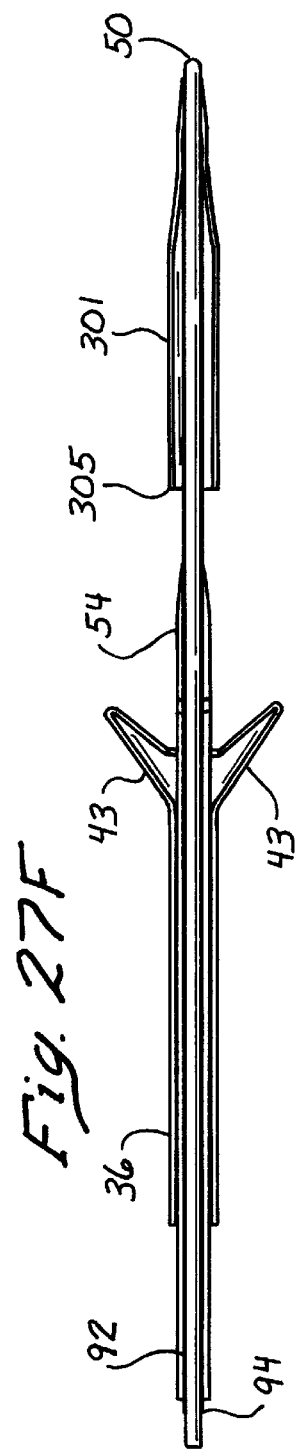

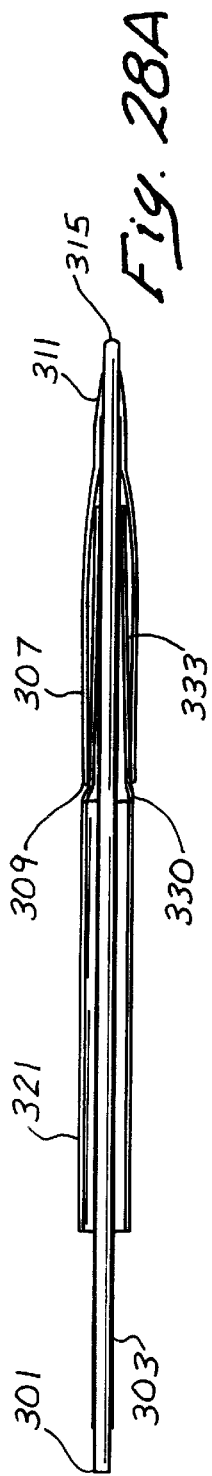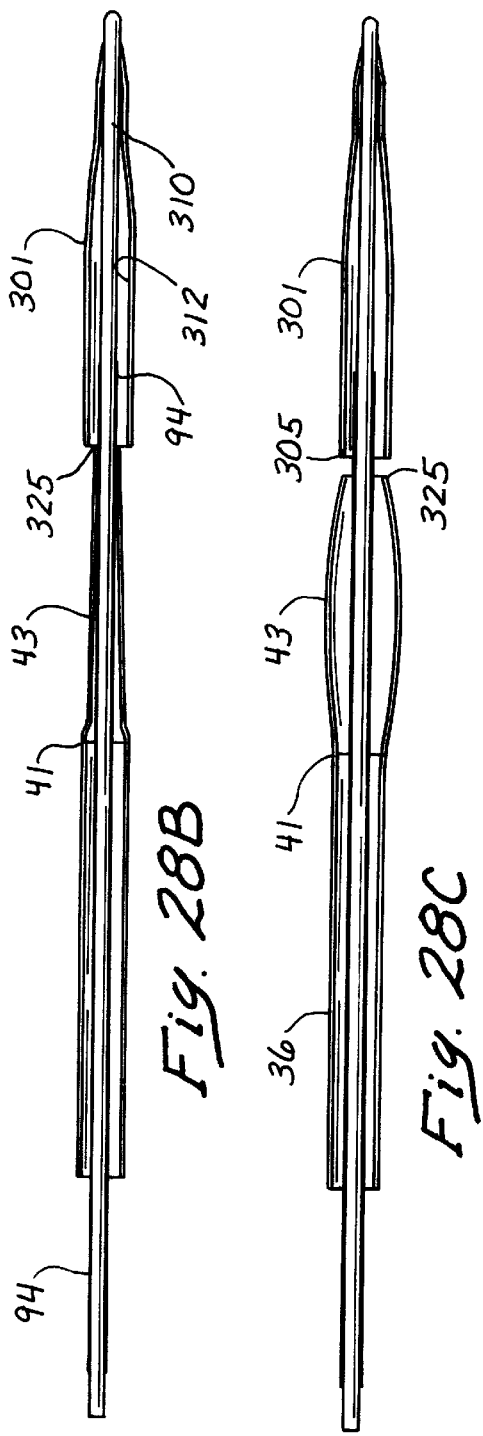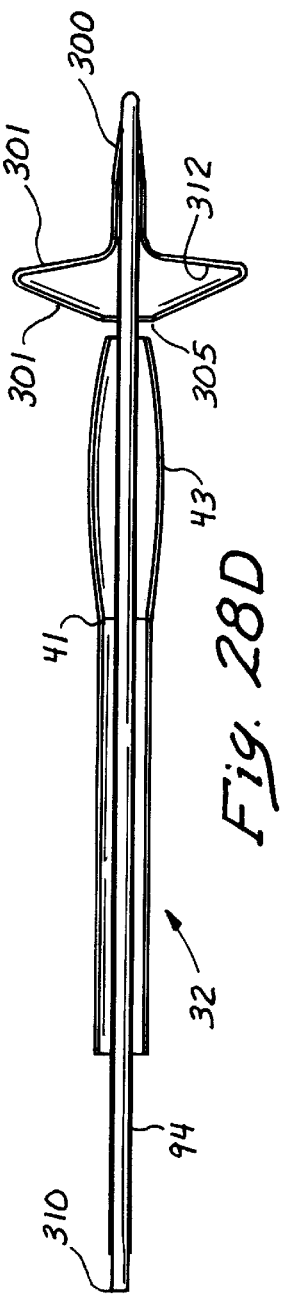

ACCESS DEVICE WITH EXPANDABLE
CONTAINMENT MEMBER

BACKGROUND OF THE INVENTION

The present invention relates generally to devices for removing obstructing material from body passages and, more particularly, to an access device configurable between a first small diameter for initial insertion into a body passage and a second larger diameter for effecting the removal of obstructing material.

The prior art includes many devices for removing obstructing material from body passages. When the body passage comprises a blood vessel, obstructing materials may include plaque, thrombus, embolus, clots, and fatty deposits. In other cases, obstructions may result from stones and strictures.

Catheters are commonly inserted into vessels for the purpose of dislodging obstructing materials from the vessel walls. In a prevalent technique commonly referred to as an embolectomy/thrombectomy procedure, a balloon tipped catheter is introduced through a surgical incision and into a blood vessel. The balloon tipped catheter is advanced to the location of the obstructing material or occlusion, and the balloon is then inflated at a point within the vessel beyond the point of the obstructing material. The catheter including the attached balloon is then pulled back to the point of insertion. In this manner, the balloon pushes the obstructing material to the point of insertion where it is removed through the incision. When the obstructing material is detached from a vessel wall using this technique, the obstructing material will often have a tendency to disperse and migrate with the flow of blood within the vessel. This dispersion can make collection and removal of the obstructing material difficult, and the migration can put the patient at risk of acute trauma. Thus, a problem associated with this embolectomy technique involves the efficient collection and removal of obstructing material while preventing migration and dispersion of the obstructing material. Other percutaneous procedures exist in the prior art for recanalization of vessels. One percutaneous procedure involves the use of laser energy to vaporize the stenotic material. Another percutaneous procedure, commonly referred to as aspiration embolectomy/thrombectomy, relies on a negative pressure to collect the obstructing material.

Percutaneous or minimally invasive access to a blood vessel in the case of a balloon catheter, for example, requires the catheter to have a very small diameter to fit through a corresponding small incision in the blood vessel. Once the catheter is in the blood vessel, however, portions of the catheter need to assume a large profile removal interface for efficient removal of the obstructing material from the lumen of the blood vessel.

In an attempt to meet this dual functional requirement of small incision diameter and large intraluminal operating diameter, the prior art has incorporated sheaths in conjunction with catheters. U.S. Pat. No. 5,011,488 to Ginsburg discloses the use of an expanding funnel-shaped sheath for use in withdrawing thrombus or embolus (obstructing material) from a blood vessel. The funnel is deployed by extending the expanding funnel-shaped sheath from within a second sheath to thereby allow the compressed funnel to expand radially. Use of this second sheath tends to increase the overall diameter of the device, thus increasing the size of the incision required for insertion of the device. In addition to not achieving an optimally small insertion diameter, this device is also unable to obtain an optimally large intraluminal operating diameter. An optimally large intraluminal operating diameter would allow for better insertion and removal of larger instruments through the sheath. This prior art technique of inserting both the introducer sheath and the pre-shaped funnel sheath into the body passage, and of subsequently removing the introducer sheath, requires the large introduction incision to form a seal around the smaller diameter pre-shaped funnel sheath after the introducer sheath is removed. In other words, the double sheath combination of the prior art requires an initial incision into the body passage large enough to accommodate the introducer sheath and, subsequently, small enough to adequately form a seal around the smaller pre-formed funnel sheath left in place after the introducer sheath is removed. Since the initial incision cannot be subsequently reduced in size to accommodate the funnel sheath, a good seal in this prior art system is difficult to obtain.

Other devices, which provide access to relatively inaccessible regions of blood vessels, are disclosed in U.S. Pat. No. 4,530,698 and U.S. Pat. No. 4,437,859. Needle and sheath combinations for use in drug delivery, blood withdrawal, and dialysis have been proposed by the prior art, but these devices incorporate different structure to solve a problem, which is different than the removal of obstructing material from a body passage. U.S. Pat. No. 5,234,425 to Fogarty discloses a variable diameter sheath constructed of a composite elastomeric material that may be stretched to reduce the diameter. This variable diameter sheath, however, is not used for the removal of obstructing material. Instead, the primary goal of this device is to provide a lining of a body passage with a thin walled single thickness interior sheath, which is introduced into the body passage in a reduced diameter condition and subsequently expanded to snugly fit the interior wall of the body passage. The variable diameter sheath incorporates a tubular braid encapsulated within a coating of high elongation silicone polymer. None of the prior art devices disclose a sheath, which is efficiently configurable between a minimum diameter and a maximum diameter, and which comprises a lumen for accommodating a catheter to facilitate removal of obstructing material from a body passage.

SUMMARY OF THE INVENTION

The access device of the present invention does not require an initial large incision to subsequently form a seal around a smaller-diameter funnel shaped sheath. The access device of the present invention is insertable into a body passage or duct using a minimally invasive technique. A distal portion of the access device of the present invention may be enlarged in diameter, while the diameter of the portion contacting the incision area of the blood vessel remains constant. The access device fits through an optimally small incision within the blood vessel, and the portion of the access device contacting the incision area of the blood vessel does not change in diameter, thus providing an effective seal.

The enlarged diameter of the distal portion of the access device may comprise any of a variety of predetermined shapes and sizes, depending upon the specific needs required by a given procedure. According to one feature of the present invention, the distal end of the access device may assume the shape of a forward facing funnel to provide a mechanism for withdrawing obstructing material from the body passage.

According to one aspect of the present invention, a single sheath having an optimally minimum diameter is inserted through an incision in a body passage. The single sheath of the access device is inserted into the body passage incision with the expandable containment member of the access device in a minimum diameter configuration. The expandable containment member is held in the minimum diameter configuration using structure other than the large-diameter external sheath of the prior art. The structure used by the present invention for configuring the expandable containment member to a minimum diameter can subsequently be removed from the lumen of the access device, once the expandable containment member has been expanded. Thus, in contrast to the prior art, the mechanism for configuring the expandable containment member does not increase the outside diameter of the access device. When the structure for configuring the expandable containment member in the small diameter configuration is no longer needed, it can be removed from the body passage without affecting the outside diameter of the access device near the incision in the body passage.

According to one aspect of the present invention, the access device includes an outer tube having a proximal tube end and a distal tube end, and a lumen extending between the proximal tube end and the distal tube end. An obturator assembly having a proximal obturator end and a distal obturator end is removably and concentrically disposed within the lumen of the outer tube. An expandable containment member having a proximal member end and a distal member end is connected to both the distal tube end and the distal obturator end. The proximal member end is connected to the distal tube end, and the distal member end is detachably connected to the distal obturator end. The expandable containment member can be expanded by relative movement between the proximal member end and the distal member end. This relative movement corresponds to relative movement of the outer tube and the obturator assembly in opposite directions. During insertion of the access device into a body passage, the proximal member end of the expandable containment member is held away from the distal member end of the expandable containment member, to thereby hold the expandable containment member in an unexpanded state. After the access device is inserted into the body passage, the proximal member end and the distal member end are moved together to expand the expandable containment member. The obturator assembly can then be removed from the access device, to thereby provide an unobstructed lumen within the outer tube. The lumen of the outer tube can then facilitate insertion and removal of instruments and materials. For example, a therapeutic balloon catheter can be inserted into the lumen to facilitate removal of embolus or thrombus. The access device of the present invention further includes a guidewire, which is adapted to be inserted through the obturator assembly. The guidewire acts as a stiffener and as a leader for the access device.

According to another feature of the present invention, the outer tube of the access device has a predetermined outer diameter and an axis extending between the proximal tube end and the distal tube end. The expandable containment member is attached to the outer tube at the distal tube end, and has an unexpanded diameter that is proximally equal to the outer diameter of the outer tube. The outer tube may include a solid walled tubular member, and the expandable containment member may include a braided tubular component. The solid walled tubular member and the expandable containment member are joined together by bonding or fusion, and the expandable containment member may be coated with a non-permeable elastomeric material that forms a barrier to flow within the body passage when the expandable containment member is expanded.

The obturator assembly of the present invention is initially connected to the expandable containment member to facilitate insertion of the access device into the body passage. The obturator assembly is disconnected from this expandable containment member after insertion of the access device, to thereby facilitate movement of the obturator assembly within the expandable containment member. The obturator assembly of the present invention includes an intermediate slidable obturator sleeve having a proximal intermediate sleeve end and a distal intermediate sleeve end. A lumen extends between the proximal intermediate sleeve end and the distal intermediate sleeve end. An inner fixed obturator sleeve has a proximal inner sleeve end and a distal inner sleeve end, and is concentrically disposed within the lumen of the intermediate slidable obturator sleeve. The obturator further includes an obturator expandable cone, which has a proximal cone end and a distal cone end. The distal cone end is connected to the distal inner sleeve end, and the proximal cone end is connected to the distal intermediate sleeve end. The obturator expandable cone can be expanded by relative movement between the proximal cone end and the distal cone end, which is affected by relative movement of the distal inner sleeve end and the distal intermediate sleeve end in opposite directions. Once the obturator expandable cone has been expanded, the obturator is moved proximally against the expandable containment member, to thereby compress the expandable containment member about an axis of the expandable containment member. The expandable containment member bends about a mid-point of the expandable containment member located between the proximal member end and the distal member end. The expandable containment member forms a cone when the proximal member end is moved sufficiently close to the distal member end, and when the distal member end is moved proximally past the mid-point of the expandable containment member.

According to the method of removing an obstructing material from a body passage of the present invention, a tubular access device is inserted into the body passage, and the tubular access device is moved in a distal direction within the body passage to a first location where obstructing material is located within the body passage. The distal end of the expandable containment member is moved toward the proximal end of the expandable containment member, to thereby expand the expandable containment member into a cone shape having a relatively large diameter. The obturator assembly of the access device is removed from the lumen of the outer tube, and a therapeutic catheter is inserted into the outer tube, and moved in the distal direction past the first location within the body passage, to a second location on the distal side of the obstructing material. The therapeutic catheter is expanded, and is then retracted in a proximal direction from the second location toward the expandable containment member. Movement of the expanded therapeutic catheter in the proximal direction transports the obstructing material into the expandable containment member and then into the lumen of the outer tube. Once the obstructing material is removed from the lumen of the outer tube and the therapeutic catheter is removed from the lumen, the obturator assembly is inserted back into the lumen of the outer tube and used to collapse the expandable containment member into a low-diameter configuration. The access device is then removed from the body passage with the expandable containment member in the low-profile configuration.

The present invention, together with additional features and advantages thereof, may best be understood by reference to the following description taken in connection with the accompanying illustrative drawings.

BRIEF DESCRIPTION OF THE DRAWINGS

FIG. 2 is a side view of the sheath assembly according to the presently preferred embodiment;

FIG. 3 is a side view of the obturator assembly according to the presently preferred embodiment;

FIG. 4 is a cross-sectional view of the access device in the introductory profile and unexpanded condition according to the presently preferred embodiment;

FIG. 5 is a cross-sectional view of the deployed access device showing the obturator expandable cone expanding the expandable containment member of the access device according to the presently preferred embodiment;

FIG. 6 is a cross-sectional view of the deployed access device showing the obturator expandable cone in an unexpanded condition according to the presently preferred embodiment;

FIG. 7 is a view of access device with the obturator removed and with the expandable containment member fully deployed according to the presently preferred embodiment;

FIG. 8 is a side view of the access device with the obturator assembly removed and the expandable containment member deployed;

FIG. 9 is a cross-sectional view of a first alternative embodiment of the present invention in the introductory profile;

FIG. 10 is a cross-sectional view of the first alternative embodiment of the present invention showing the expandable containment member partially deployed;

FIG. 11 is a cross-sectional view of the first alternative embodiment of the present invention showing the expandable containment member fully deployed;

FIG. 12 is a cross-sectional view of the first alternative embodiment of the present invention with the obturator assembly removed and the expandable containment member fully deployed;

FIGS. 27A–J are cross-sectional sequential views of a fourth alternative embodiment of the present invention showing the sequence of deployment of an expandable containment member; and FIGS. 28A–H are cross-sectional sequential views of a fifth alternative embodiment of the present invention showing the sequence of deployment of an expandable containment member.

DETAILED DESCRIPTION OF THE PRESENTLY PREFERRED EMBODIMENTS

Figure 1:
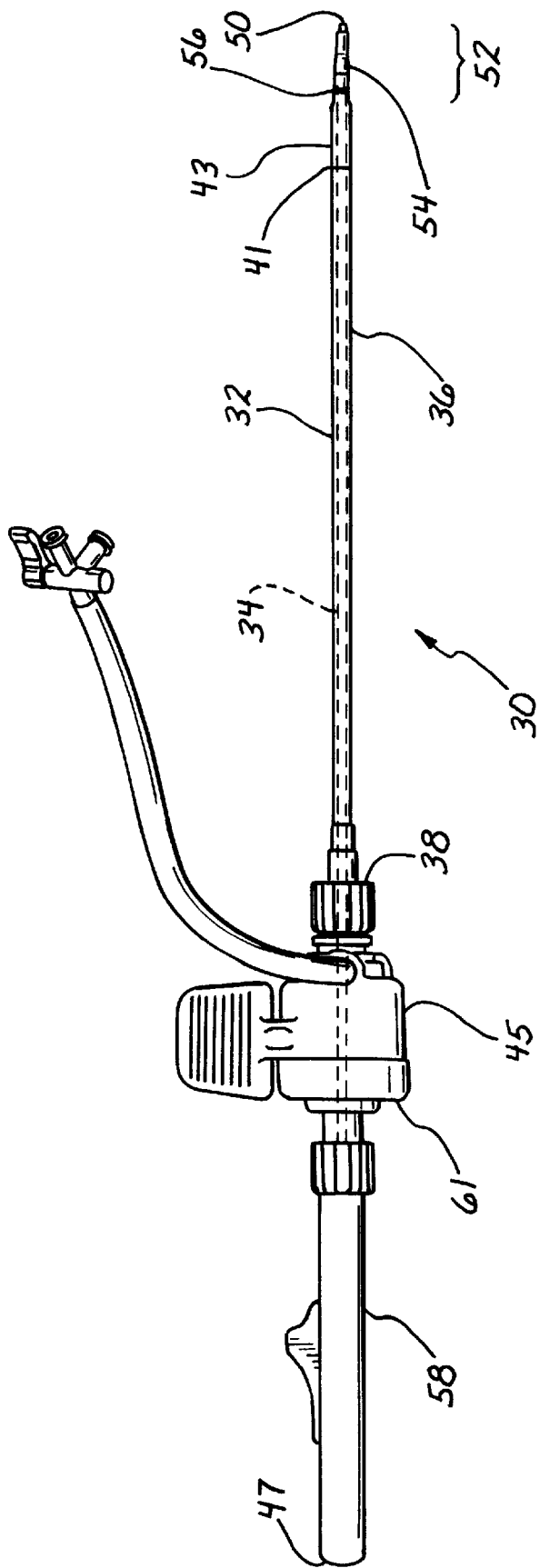
FIG. 1 is a side view of the assembled access device according to the presently preferred embodiment.

Turning to FIG. 1, an access device 30 of the present invention is illustrated having a sheath assembly 32, as best seen in FIG. 2, and an obturator assembly 34, as best seen in FIG. 3, inserted through the sheath assembly 32. The sheath assembly 32 comprises an outer flexible tube 36 having a proximal tube end 38 and a distal tube end 41. The sheath assembly 32 further comprises an accessory device 45 and an expandable containment member 43, which is connected to the outer flexible tube 36 near the distal tube end 41. The obturator assembly 34 comprises a proximal obturator end 47 and a distal obturator end 50. The obturator end area 52 includes an obturator expandable cone 54 and a proximal portion 56. The expandable containment member 43 of the sheath assembly 32 is connected to the proximal portion 56 of the obturator end area 52. An obturator handle 58 of the obturator assembly 34 is connected to the accessory device 45 of the sheath assembly 32 via a handle connector 61.

Turning to FIG. 2, the outer flexible tube 36 of the sheath assembly 32 comprises the expandable containment member 43 and a connector portion 63. The portion of the outer flexible tube 36 located between the expandable containment member 43 and the connector portion 63 preferably comprises a semi-rigid portion of solid walled tubing, and the expandable containment member 43 preferably comprises a braided tubular component. The expandable containment member 43 is preferably joined to this solid walled tubular member by either bonding or fusion. As presently embodied, the expandable containment member 43 is bonded to the solid walled tubular portion using thermal fusion. The connector portion 63 preferably comprises a solid plastic component, which is connected to the solid walled tubular portion of the outer flexible tube 36. The connector portion 63 removably connects the outer flexible tube 36 to the tube connector 67 of the accessory device 45. In the presently preferred embodiment, the connector portion 63 comprises threads (not shown) which fit into the tube connector 67 for a snug fit.

A lumen is formed within the outer flexible tube 36 between the distal tube end 41 and the proximal tube end 38. This lumen is preferably sized and configured to accommodate a shaft portion of the obturator assembly 34 (FIG. 3). The lumen of the outer flexible tube 36 may also removably accommodate other instruments. A side port 70 of the sheath assembly 32 is adapted for applying/removing air or fluid to/from the lumen of the outer flexible tube 36, under either positive or negative pressure. Instruments, such as the obturator assembly 34 (FIG. 3) can be inserted through the handle connector 61 of the sheath assembly 32 and out of the expandable containment member 43, for example. Finger tabs 71 of the accessory device 45 operate to open and seal access to the lumen of the outer flexible tube 36, depending on the configuration of the two finger tabs 71.

As shown in FIG. 3, the obturator assembly 34 comprises an obturator shaft 72, which comprises the obturator end area 52 and which is connected to the obturator handle 58 via a connector portion 74. The obturator expandable cone 54 can be radially expanded and contracted by movement of the slidable actuator 76. According to the presently preferred embodiment, the distal obturator end 50 of the obturator assembly 34 is inserted through the handle connector 61 of the sheath assembly 32. The distal obturator end is then moved through the lumen of the outer flexible tube 36, and out of the expandable containment member 43 of the sheath assembly 32. As presently embodied, the connector portion 74 of the obturator assembly 34 accommodates threads of the handle connector 61 therein. When the handle connector 61 of the sheath assembly 32 is secured within the connector portion 74 of the obturator assembly 34, the obturator end area 52 extends distally out of the expandable containment member 43 of the sheath assembly 32.

FIG. 4 is a cross-sectional view of the access device 30 of the present invention configured in an introductory profile, unexpanded condition. The lumen 78 of the outer flexible tube 36 is shown having a guidewire 81 inserted therethrough. The guidewire 81 operates as both a stiffener and a leader for the access device 30, during insertion of the access device 30 into a body passage, for example. The guidewire 81 provides strength to the access device 30, and allows for manufacturing of the outer flexible tube 36 and the obturator shaft 72 components in lightweight and thin-walled constructions in order to conserve space within the body passage. The use of the guidewire 81 also serves to reduce the strength requirements of the outer flexible tube 36 and the obturator shaft 72 components during insertion and deployment of the expandable members 43 and/or 54.

The expandable containment member 43 comprises a proximal member end 83 and a distal member end 85. The proximal member end 83 of the expandable containment member 43 is preferably bonded to the solid walled portion of the flexible tube 36, and the distal member end 85 of the expandable containment member 43 is bonded, via a bonded portion 87, around the obturator shaft 72.

The outer slidable obturator sleeve 90 is preferably fused to the distal member end 85 of the expandable containment member 43 at the bonded portion 87. As presently embodied, the outer slidable obturator sleeve 90 is fused to the tubular mesh of the expandable containment member 43 by heating the outer flexible tube 36 and the expandable containment member 43 while holding them in compression and over an inserted mandrel. This construction results in no substantial buildup of material in the bonded portion 87 and a minimum increase of diameter in the bonded portion 87. In order to maintain the tight tolerances required for optimum use of space in the device, the outer flexible tube 36 material is forced to flow into the woven material of the expandable containment member 43 and into and around the individual woven elements thereof. The woven material of the expandable containment member 43 is subsequently folded back to form a bending area 107 in the woven mesh of the expandable containment member 43, and extended proximally to overlap the distal tube end 41 of the outer flexible tube 36. The proximal member end 83 of the expandable containment member 43 is fused to the outer flexible tube 36 in a similar manner.

The obturator shaft 72 comprises an outer slidable obturator sleeve 90, an intermediate slidable obturator sleeve 92, and an inner fixed obturator sleeve 94. The guidewire 81 fits within the inner fixed obturator sleeve 94. The outer flexible tube 36 of the sheath assembly 32 fits around the outer slidable obturator sleeve 90. A portion of the outer slidable obturator sleeve 90 is recessed at the bonded portion 87 to thereby accommodate the distal member end 85 of the expandable containment member 43 within this recessed portion of the outer slidable obturator sleeve 90. The outer slidable obturator sleeve 90 continues distally of the expandable containment member 43 as the obturator end area 52. More particularly, the outer slidable obturator sleeve 90 at the obturator end area 52 comprises a solid walled portion 97, the obturator expandable cone 54, and a distal solid walled portion 99. The obturator expandable cone 54 preferably comprises a woven tubular structure, which may be similar to the braided material of the expandable containment member 43. The obturator expandable cone 54 is preferably fused between the solid walled portion 97 and the distal solid walled portion 99 of the outer slidable obturator sleeve 90, at the proximal fuse location 101 and the distal fuse location 103, respectively. The bonded portion 87 of the outer slidable obturator sleeve 90 holds the expandable containment member 43 in place during insertion of the access device 30 into a body passage. After the access device 30 is positioned within the body passage, the obturator shaft 72 may be moved distally, relative to the sheath assembly 32, to thereby release the bonded portion 87 from within the recess of the outer slidable obturator sleeve 90.

A purpose of the outer slidable obturator sleeve 90, the intermediate slidable obturator sleeve 92, and the inner fixed obturator sleeve 94 is to facilitate relative movement between the proximal fuse location 101 and the distal fuse location 103 of the outer slidable obturator sleeve 90, without requiring movement of the guidewire 81. In other words, the guidewire 81 is slidably contained within the inner fixed obturator sleeve 94. A distal end of the intermediate slidable obturator sleeve 92 is connected to the solid walled portion 97 of the outer slidable obturator sleeve 90, and a distal end of the inner fixed obturator sleeve 94 is connected to the distal solid walled portion 99. Since the distal end of the inner fixed obturator sleeve 94 is connected to the distal solid walled portion 99 and the distal end of the intermediate slidable obturator sleeve 92 is connected to the solid walled portion 97, movement of these two distal ends relative to one another results in movement of the two ends 101, 103 of the obturator expandable cone 54.

As shown in FIG. 5, the distal end of intermediate slidable actuator sleeve 92 may be moved toward the distal end of the inner fixed obturator sleeve 94, to thereby move the proximal fuse location 101 toward the distal fuse location 103.

In FIG. 5, the distal end of the inner fixed obturator sleeve 94 has been moved proximally toward the distal end of the intermediate slidable obturator sleeve 92, and the obturator expandable cone 54 has increased in radial diameter. The entire obturator shaft 72 is then moved proximally, in order to move the distal member end 85 of the expandable containment member 43 toward the proximal member end 83 of the expandable containment member 43. As presently embodied, both the proximal portion 56 of the obturator end area 52 and the obturator expandable cone 54 press proximally against the expandable containment member 43, to thereby move the distal member end 85 about a bending area 107 of the expandable containment member 43. The bending area 107 approximately bisects the length of the expandable containment member 43, and allows further movement of the obturator expandable cone 54 in the proximal direction to configure the expandable containment member 43 into a cone shape. In this cone shape, a distal portion of the expandable containment member 43 comprises an inner surface 108 of the cone and the bending area 107 forms an enlarged distally facing rim of the cone.

The inside surface 108 of the expandable containment member 43 thus folds into the outside surface 110 about the bending area 107, to form a cone. This folding action occurs at a point near the expansion limit of the woven mesh of the expandable containment member 43. The cone thus formed comprises a double-wall structure having an outer surface 110 and an inside surface 108 and a space therebetween forming a truss. The large distally facing rim 107 of the cone is adapted for intimate contact with intimal tissue within a body passage, for example. This bending area 107 comprises folded elements of mesh of the expandable containment member 43 which greatly increase the hoop strength of the cone while, at the same time, presenting a relatively atraumatic distal feature without any exposed mesh element ends extending therefrom.

After the expandable containment member 43 is configured into the cone shape, the obturator shaft 72 of the obturator assembly 34 is moved distally away from the cone, as illustrated in FIG. 6. Additionally, the distal end of the inner fixed obturator sleeve 94 is moved away from the distal end of the intermediate slidable obturator sleeve 92, to thereby collapse the obturator expandable cone 54. After the obturator, expandable cone 54 has been collapsed, the obturator shaft 72 is again moved proximally. The obturator shaft 72 is moved proximally until the entire obturator assembly 34 is removed from the lumen 78 of the outer flexible tube 36. Additionally, the guidewire 81 is removed from the lumen 78.

FIG. 7 illustrates the outer flexible tube 36, with the expandable containment member 43 configured into the cone shape, having an enlarged distally facing rim 107. The lumen 78 is free for subsequent introduction of other instruments, such as a therapeutic balloon catheter. FIG. 8 illustrates the entire sheath assembly 32 with the obturator assembly 34 (FIG. 3) removed therefrom and the expandable containment member 43 shaped into a cone.

FIGS. 9–12 illustrate an alternative embodiment of the present invention where the obturator shaft 112 comprises a single tube, which accommodates a guidewire 114. The obturator shaft 112 slidably fits within an outer flexible tube 116, which comprises an expandable containment member 118. A distal end 121 of the expandable containment member 118 is fused or bonded to the connection area 123. As shown in FIG. 10, when the obturator shaft 112 is moved proximally, the distal end 121 of the expandable containment member 118 is moved toward the proximal end 125 of the expandable containment member 118. The expandable containment member 118 expands and bows outwardly about the bending areas 127.

As with the embodiment discussed above with reference to FIGS. 4–7, the distal end 130 of the guidewire 114 can remain stationary while the obturator shaft 112 and the outer flexible tube 116 are moved relative to one another. Alternatively, the distal end 121 may be mechanically connected to the connection area 123, for example.

FIG. 11 corresponds to FIG. 6, where the inner surface 132 is folded inside of the outer surface 134 and a large distally facing rim 127 forms a cone. The obturator shaft 112 in this embodiment, however, does not need to be moved distally before removal but, instead, may be moved proximally from the configuration of FIG. 11 out of the lumen 138 (FIG. 12) of the outer flexible tube 116. In the embodiment of FIGS. 4–7, the obturator shaft 72 does not need to be moved forward either, and the obturator expandable cone 54 does not need to be collapsed, before removal of the obturator shaft 72 from the lumen 78. The embodiment of FIGS. 4–7, however, may benefit from the collapsing of the obturator expandable cone 54 before removal of the obturator shaft 72. It is noted that a preferred operation of the embodiment of FIGS. 4–7 involves moving the distal ends of the intermediate slidable obturator sleeve 92 and the inner fixed obturator sleeve 94 away from one another, to thereby apply tension to the obturator expandable cone 54 and reduce the profile or diameter of this obturator expandable cone 54, before removal of the obturator shaft 72.

Figure 13A:
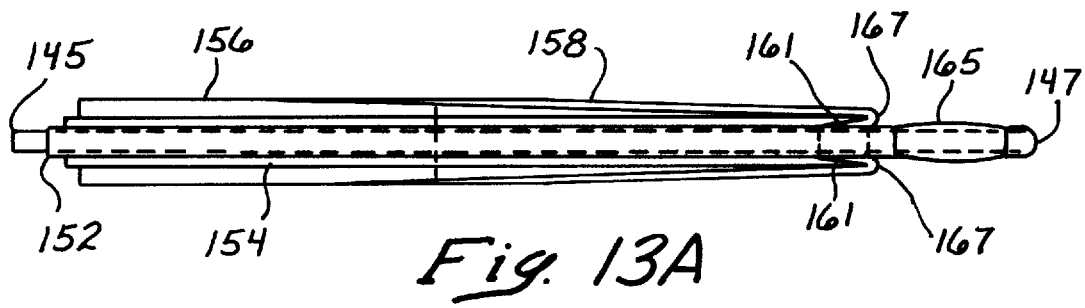
FIGS. 13A–G are cross-sectional sequential views of a second alternative embodiment of the present invention illustrating the sequence of expansion and deployment.
Figure 13B:
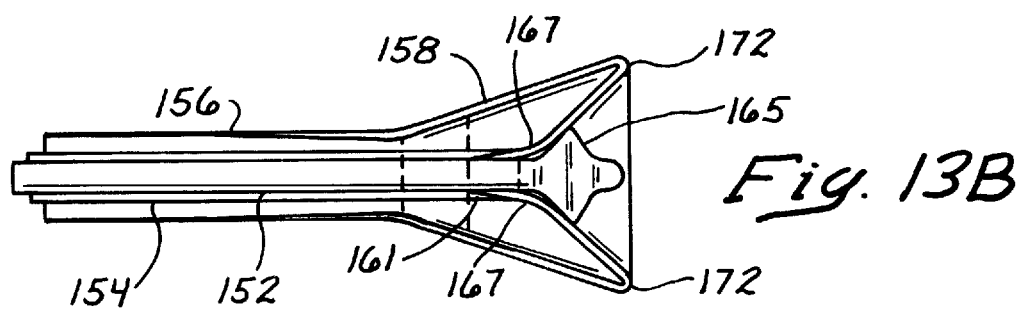
Figure 13C:
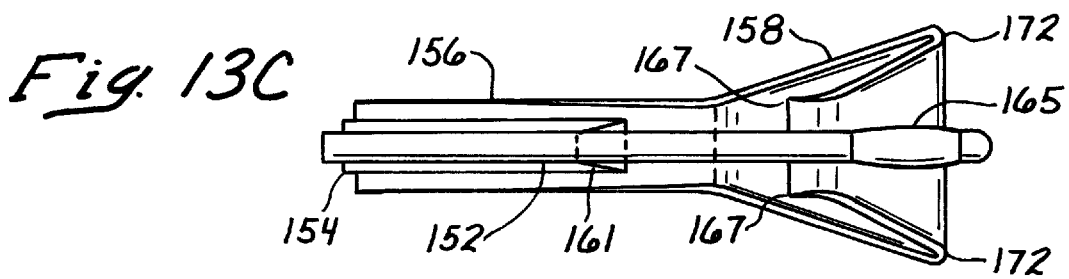

FIGS. 13A–13G illustrate another embodiment of the present invention, where a guidewire 145 having a distal end 147 is inserted within an inner slidable obturator sleeve 152. The inner slidable obturator sleeve 152 fits within an outer obturator containment sleeve 154, and the outer obturator containment sleeve 154 fits within an outer flexible tube 156 of a sheath assembly. An expandable containment member 158 is connected to the outer flexible tube 156, and is also connected to the holding ends 161 of the outer obturator containment sleeve 154. The inner slidable obturator sleeve 152 comprises an obturator expandable cone 165. During insertion of the access device into a body passage, the two holding ends 161 of the outer obturator containment sleeve 154 hold the distal ends 167 of the expandable containment member 158 in place. As shown in FIG. 13B, the obturator expandable cone 165 is then expanded and moved proximally into contact with the distal end 167 of the expandable containment member 158. The expandable containment member 158 bends about the bending portions 172 to thereby form a cone or funnel. The obturator expandable cone 165 is then collapsed, as shown in FIG. 13C, and the distal ends 167 of the expandable containment member 158 are released from the holding ends 161 of the outer obturator containment sleeve 154.

Figure 13D:
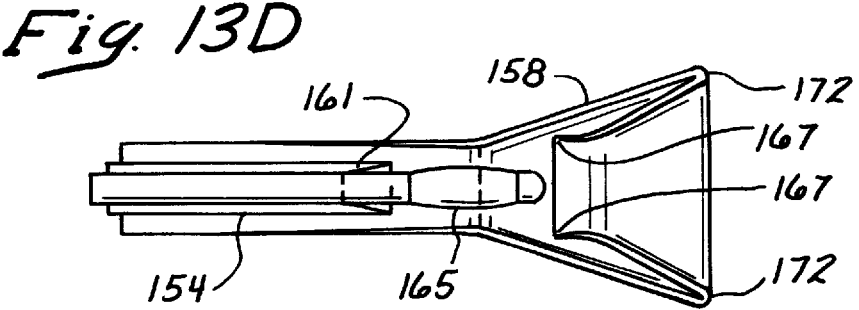
Figure 13E:
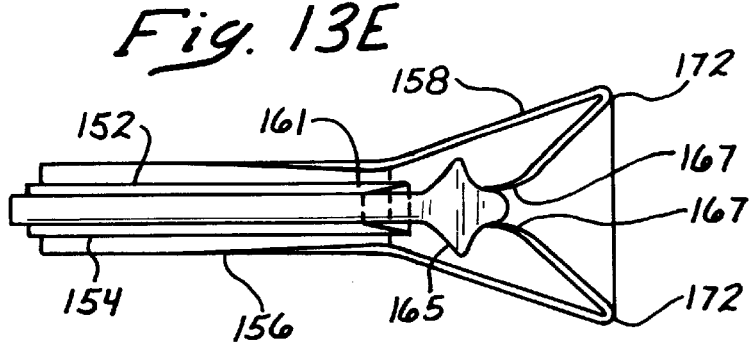
Figure 13F:
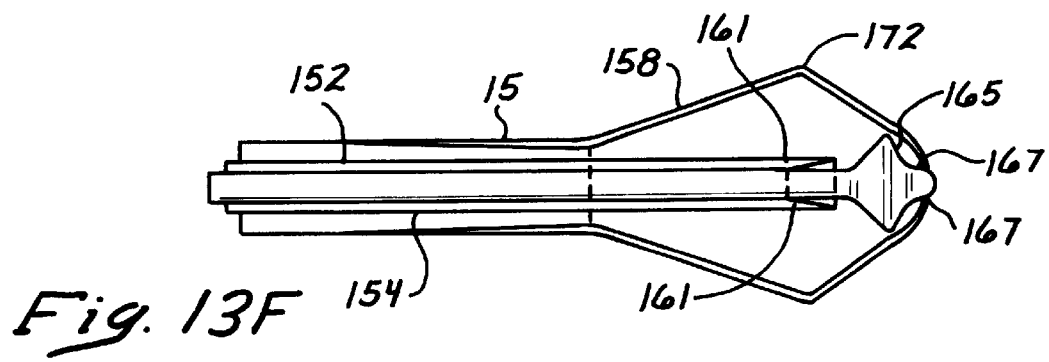
Figure 13G:
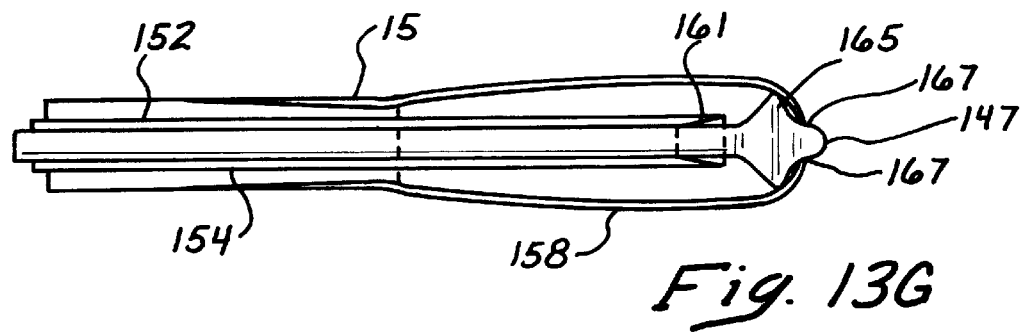

The expandable containment member 165, the outer obturator containment sleeve 154, the inner slidable obturator sleeve 152, and the guidewire 145 are then removed from the outer flexible tube 156, as illustrated in FIG. 13D. Before the access device is removed from the body passage, according to the presently preferred embodiment, the expandable containment member 158 is collapsed back into a low profile configuration. Alternatively, the outer flexible tube 156 may be removed from the body passage without collapsing the expandable containment member 158. As shown in FIGS. 13E–13G, the obturator expandable cone 165 is expanded and moved distally against the distal ends 167 of the expandable containment member 158, to thereby collapse the expandable containment member 158. FIGS. 14A–14D illustrate another embodiment of the present invention, where the obturator expandable cone of the previous embodiment is replaced with an enlarged diameter portion 178. An inner slidable obturator sleeve 181 fits within an outer obturator containment sleeve 183, and the outer obturator containment sleeve 183 fits within an outer flexible tube 185. The outer flexible tube 185 is connected to an expandable containment member 187, which comprises a distal end 190 that is held by holding ends 192 of the outer obturator containment sleeve 183.

Figure 14A:
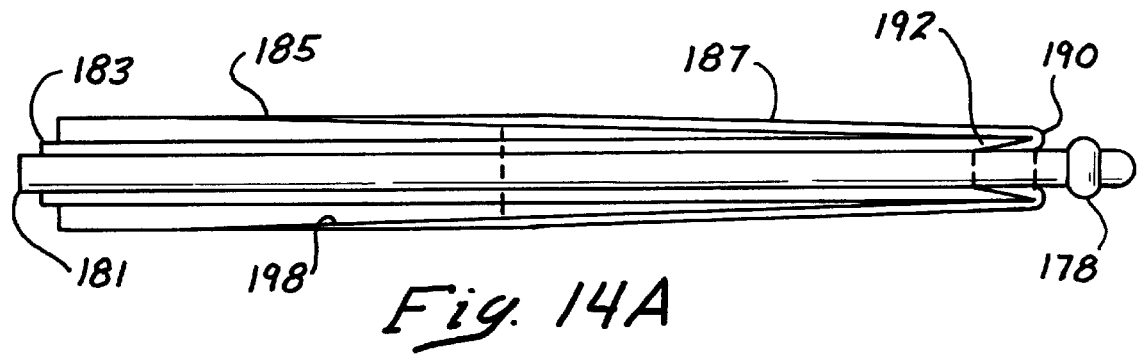
FIGS. 14A–D are cross-sectional views of a third alternative embodiment of the present invention showing the sequence of deployment of the expandable containment member.
Figure 14B:
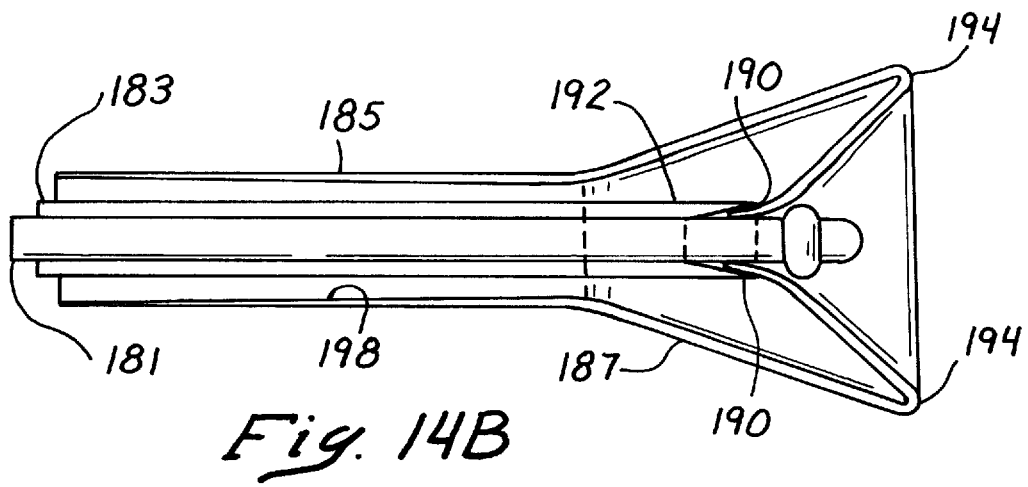
Figure 14C:
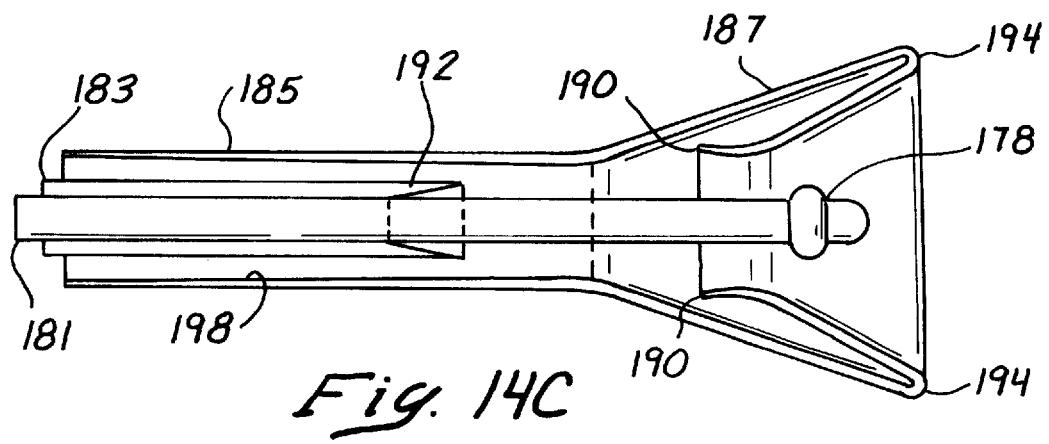
Figure 14D:
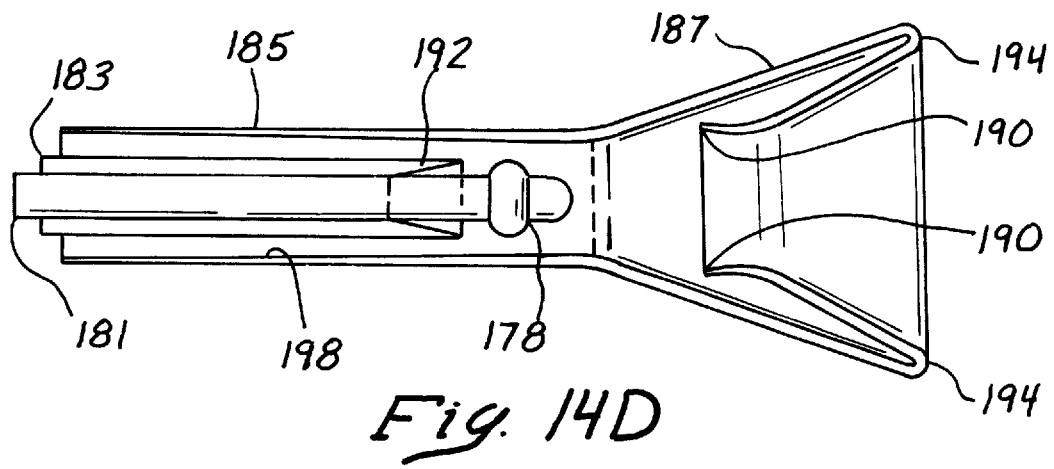

In this embodiment, proximal movement of the holding ends 192 compresses the expandable containment member 187, and moves the distal ends 190 about the bending portions 194 to thereby form a cone, as illustrated in FIG. 14B. The holding ends 192 are further moved proximally to thereby release the distal ends 190 of the expandable containment member 187, as shown in FIG. 14C. The enlarged diameter portion 178 is then moved proximally into close proximity to the holding ends 192. The inner slidable obturator sleeve 181, the outer obturator containment sleeve 183, and the enlarged diameter portion 178 are all moved proximally out of the lumen 198 of the outer flexible tube 185.

Figure 15:
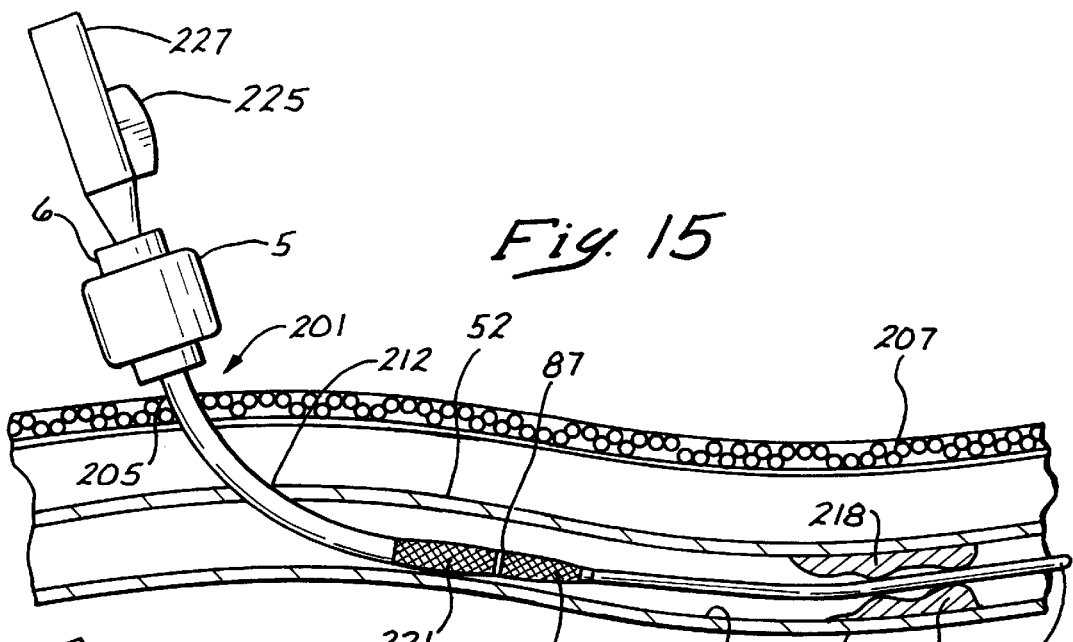
FIG. 15 is a view of the presently preferred embodiment inserted within a body passage.

The operation of the access device of the present invention is now described with reference to FIGS. 15–26. Referring to FIG. 15, an access device 201 is inserted over a placed guidewire 203 through a puncture site 205 in the skin 207 of a patient, and through a vessel puncture 212 of a body passage 214. The access device 201 is urged over the guidewire 203 to a desired area proximal of an occlusive material 218 within the lumen 219 of the body passage 214. The profiles of the expandable containment member 221 and the obturator expandable cone 223 are maintained at a minimum by maintaining tension on these members 221, 223 through the distal position of the slidable obturator 225 on the obturator handle 227. Once the access device 201 has been positioned within the lumen 219 of the body passage 214, the tension upon the expandable containment member 221 and the obturator expandable cone 223 may be released.

Figure 16:
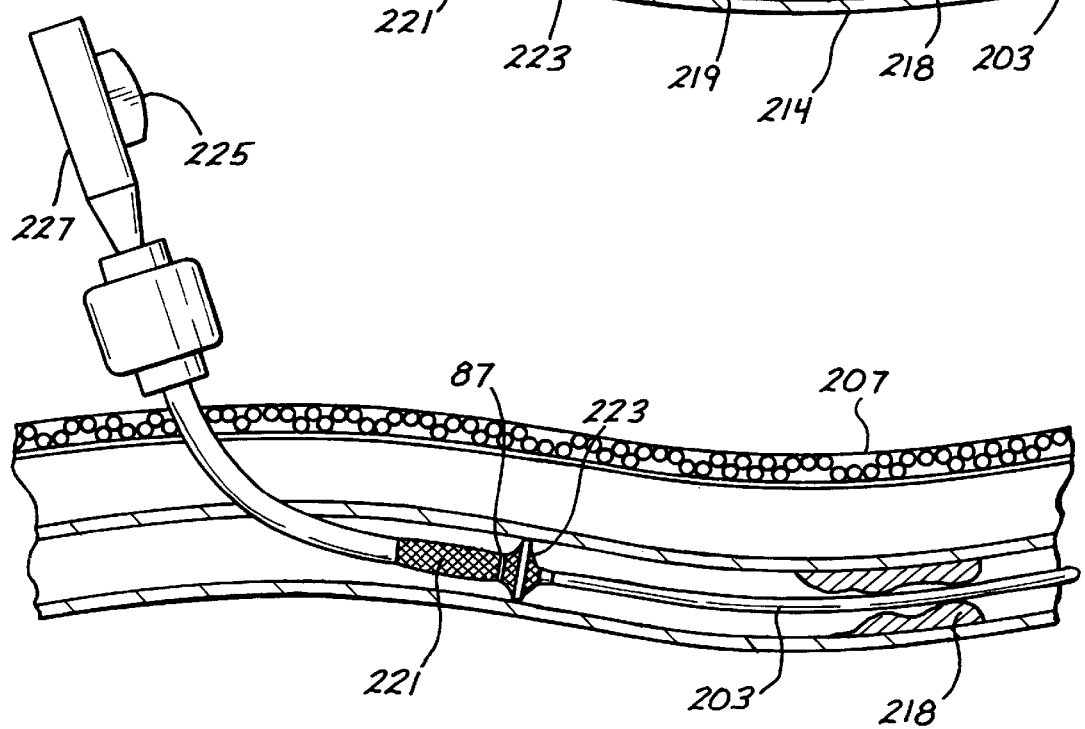
FIG. 16 is a view of the presently preferred embodiment inserted within a body passage with the obturator expandable cone deployed.
Figure 17:
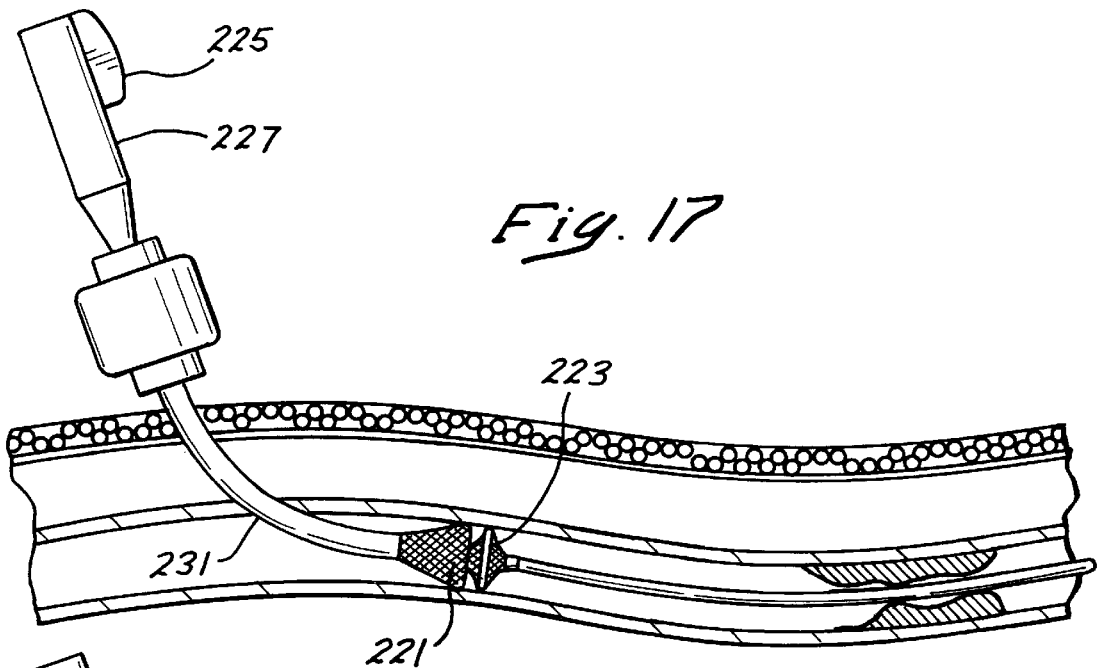
FIG. 17 is a view of the access device of the presently preferred embodiment inserted within a body passage showing the obturator assembly opening the expandable containment member.
Figure 18:
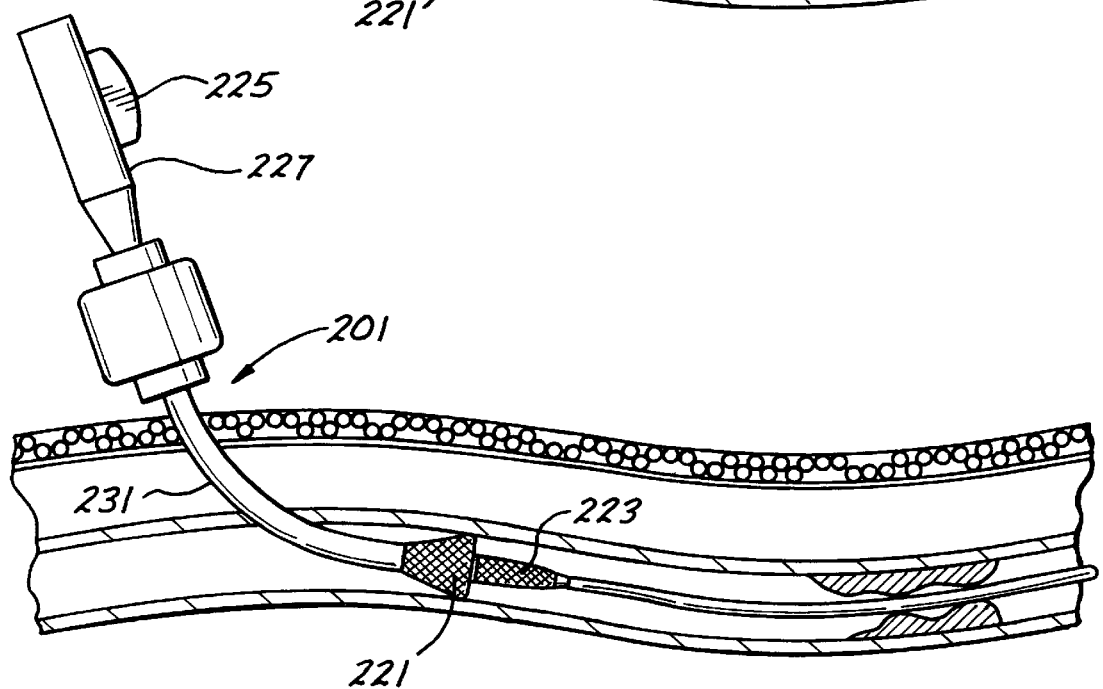
FIG. 18 is a view of the access device of the presently preferred embodiment inserted within a body passage showing the obturator assembly in the removal profile.

As shown in FIG. 16, the slidable actuator 225 is moved to a second, proximal position on the obturator handle 227 resulting in the expansion of the obturator expandable cone 223. As the obturator expandable cone 223 is pushed forward and/or urged to an expanded configuration, the bond portion 87 (as best seen in FIG. 4) is broken. The obturator expandable cone 223 is then moved proximally against the distal end of the expandable containment member 221, resulting in expansion of the expandable containment member 221. FIG. 17 illustrates how the obturator expandable cone 223 is used to urge the expandable containment member 221 into a cone shape. The fully expanded obturator expandable cone 223 is pulled proximally against the distal end of the expandable containment member 221, until this distal end of the expandable containment member 221 begins to invert. Once the expandable containment member 221 has been formed into a cone shape, the fully expanded obturator expandable cone 223 is urged proximally into the cone shape and into the outer tube 231 of the access device.

Once the expandable containment member 221 has been formed into the shape of a cone or funnel, tension is again placed onto the obturator expandable cone 223, resulting in the obturator expandable cone 223 collapsing. This tension is supplied by the slidable actuator 225 of the obturator handle 227. After the profile of the obturator expandable cone 223 has been reduced to a minimum diameter (FIG. 18), the obturator expandable cone 223 is removed from the outer tube 231 of the access device 201.

Figure 19:
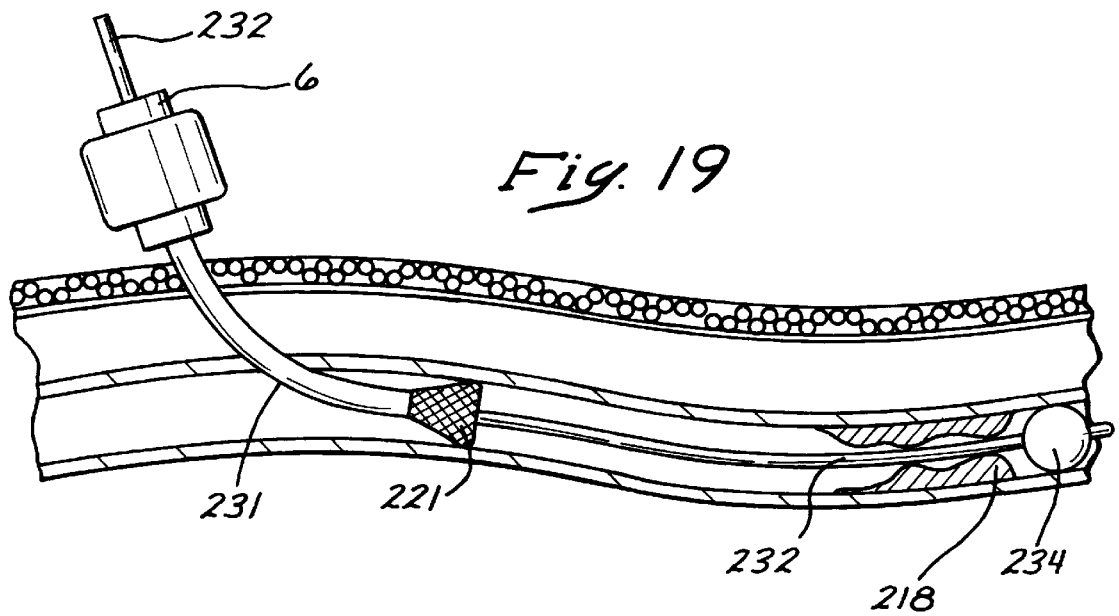
FIG. 19 is a view of the access device of the presently preferred embodiment inserted within a body passage showing the expandable containment member in the open condition with the obturator assembly removed and with a therapeutic balloon catheter inserted.
Figure 20:
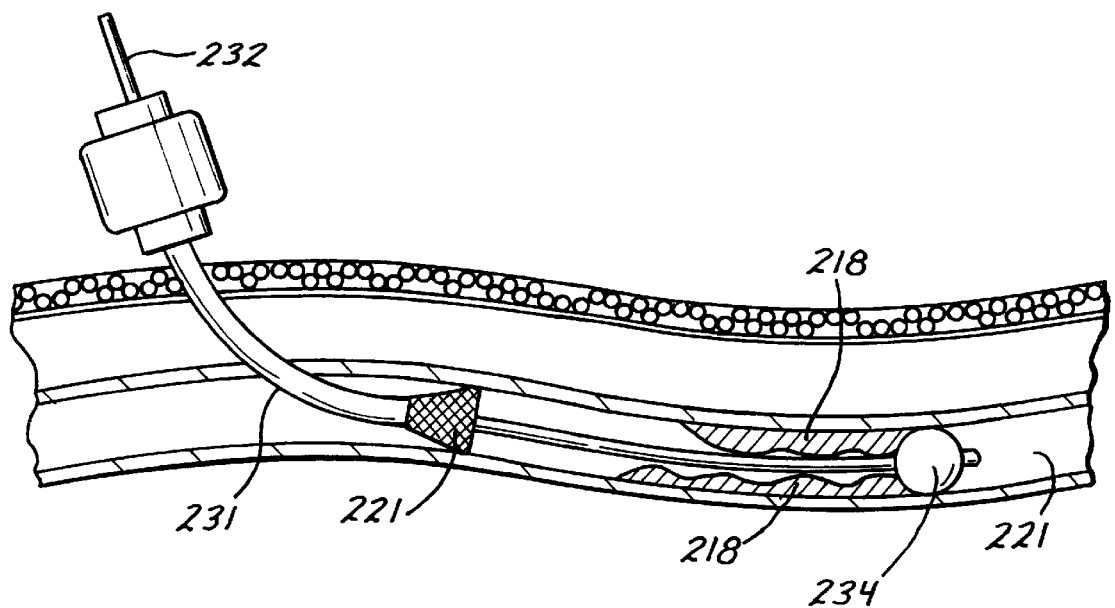
FIG. 20 is a view of the access device of the presently preferred embodiment inserted within a body passage illustrating the use of a balloon catheter through the access device to treat an occlusion.
Figure 21:
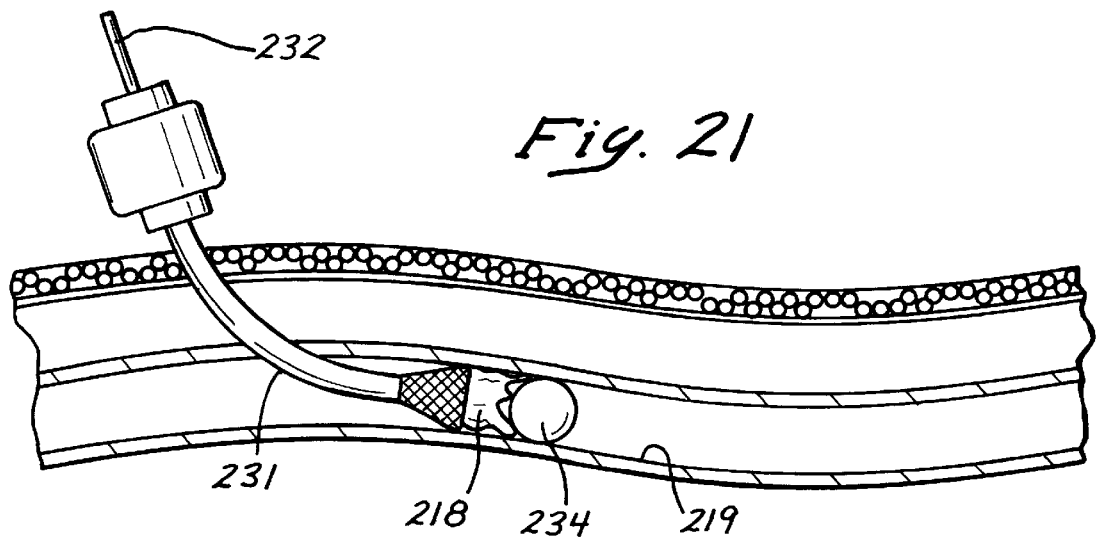
FIG. 21 is a view of the access device of the presently preferred embodiment in use within a body passage as a balloon catheter withdraws an occlusive mass toward the expandable containment member of the access device.
Figure 22:
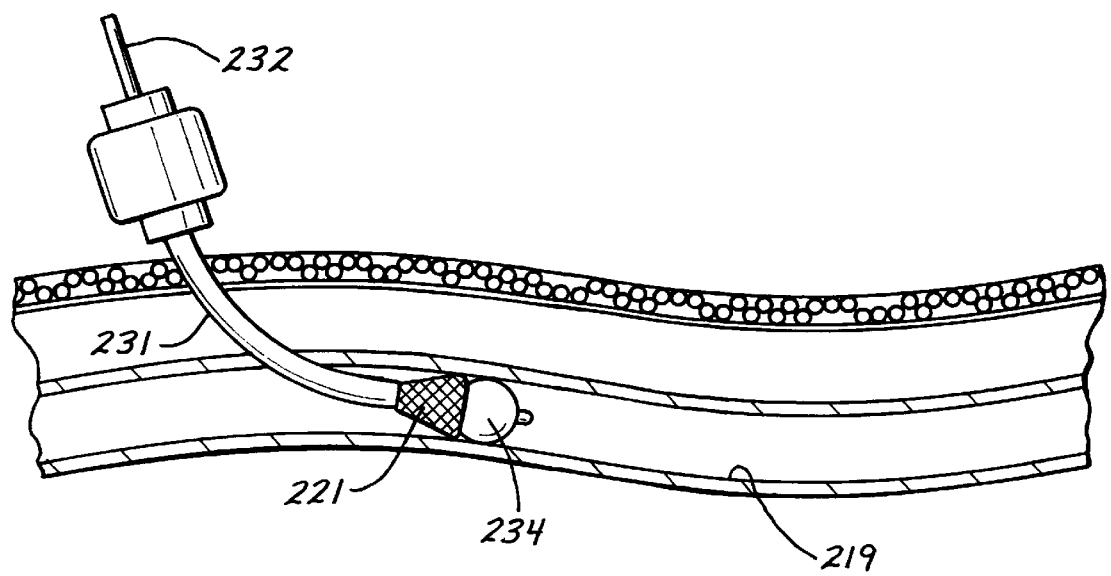
FIG. 22 illustrates the containment of an occlusive mass within the expandable containment member according to the presently preferred embodiment.
Figure 23:
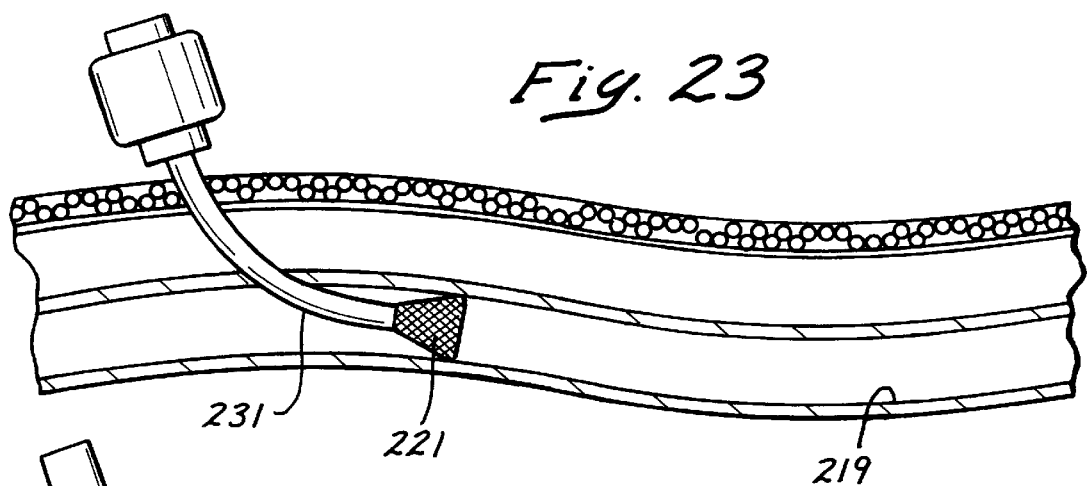
FIG. 23 is a view of the expanded containment member of the access device of the presently preferred embodiment with the balloon catheter removed.

After the obturator assembly, including the guidewire 203, is removed from the outer tube 231, a therapeutic balloon catheter 232 may be placed into the lumen of the tube 231, as shown in FIG. 19. The therapeutic balloon catheter 232 is advanced distally past the occluding material 218 before the balloon 234 is expanded. Other instruments may be inserted through the outer tube 231, as well. The therapeutic balloon catheter 232 is expanded at a distal location, relative to the occluding material 218, and the occluding material 218 is then urged proximally toward and into the enlarged opening of the funnel formed by the expandable containment member 221. As the occluding material 218 is extruded into the funnel of the expandable containment member 221, the removal process may be assisted by application of suction through the side port 70 (FIG. 2). FIG. 21 illustrates the compressing of the occluding material 218 into the expandable containment member 221 by the balloon 234 of the therapeutic balloon catheter 232. FIG. 22 shows the occluding material 218 being completely captured within the expandable containment member 221, and FIG. 23 illustrates the expandable containment member 221 and the outer tube 231 after the balloon 234 has been reduced in diameter and removed. The balloon 234 is drawn proximally through the outer tube 231, with the continued application of suction, to thereby transport the occluding material 218 out of the outer tube 231.

Figure 24:
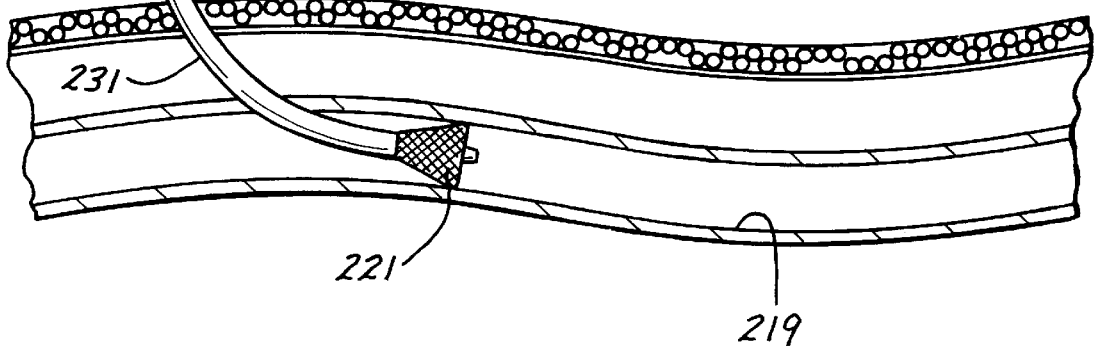
FIG. 24 is a view of the access device of the presently preferred embodiment showing the obturator assembly being re-inserted to collapse the expandable containment member for removal from the body passage.
Figure 25:
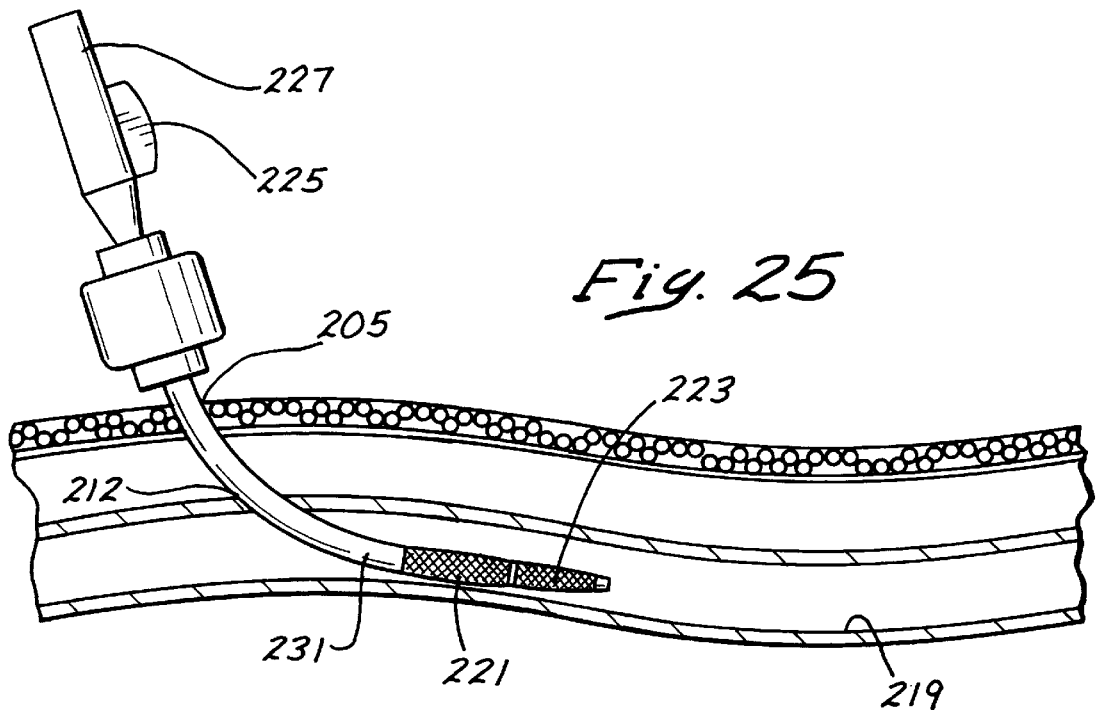
FIG. 25 is a view of the collapsed expandable containment member and obturator assembly of the presently preferred embodiment, prior to removal from a body passage.
Figure 26:
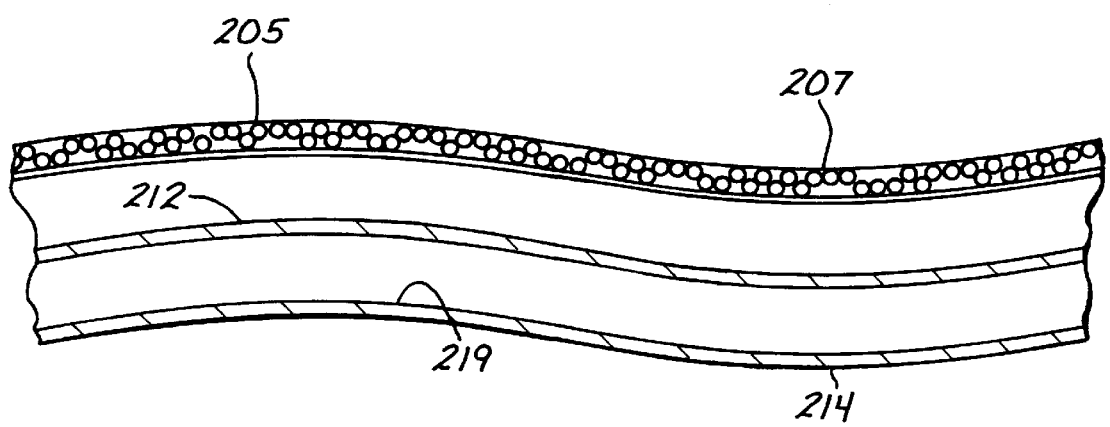
FIG. 26 is a view of a body passage with the access device of the presently preferred embodiment removed.

Once the occluding material 218 has been removed from the outer tube 231, the obturator assembly is reinserted into the outer tube 231, as illustrated in FIGS. 24 and 25. Upon reaching the proximal end of the expandable containment member 221, the obturator expandable cone 223 is expanded to engage the inverted end of the expandable containment member 221. When the obturator is further moved distally, the funnel formed by the expandable containment member 221 is reverted to a low profile configuration. Subsequently, the obturator expandable cone 223 is also reduced to a low profile configuration, as shown in FIG. 25, and the access device 201 is removed. FIG. 26 illustrates the body passage 214 and the skin 207 after removal of the access device 201 therefrom. An occlusion free lumen 219 with minimal punctures 205, 212 remains.

FIGS. 27A–J illustrate a fourth alternative embodiment of the present invention. A guide wire 301 fits within an inner-fixed obturator sleeve 303 and an outer slidable obturator sleeve 305. A reversible sheath 307 comprises a proximal sheath end 309 and a distal sheath end 311. As presently embodied, the reversible sheath 307 is secured to the distal end 315 of the guidewire 301. The outer slidable obturator sleeve 305 comprises an obturator expandable cone 317, which is connected to a distal portion of the outer slidable obturator sleeve 305. An outer flexible tube 321 fits around the outer slidable obturator sleeve 305 and the obturator expandable cone 317. The outer flexible tube 321 comprises a distal tube end 330, which is connected to an expandable containment member 333. The expandable containment member 333 fits beneath the reversible sheath 307 during insertion of the device into a body passage, for example. As presently embodied, the reversible sheath 307 comprises a braided material similar to the material comprising the expandable containment member 333.

In operation, the reversible sheath 307 covers the expandable containment member 333 so that forces acting to expand the expandable containment member 333 upon insertion into a vessel are applied to the reversible sheath 307 in a direction that compresses the material of the reversible sheath 307 rather than expand the material. After the device is in place within the body passage, the reversible sheath 307 is moved distally so that the proximal sheath end 309 of the reversible sheath 307 is beyond the distal end 350 of the expandable containment member 333, as illustrated in FIG. 27B. The reversible sheath 307 is then further moved distally to allow for deployment of the obturator expandable cone 317, as illustrated in FIG. 27C. The obturator expandable cone 317 is moved distally through a lumen formed by the expandable containment member 333, until the obturator expandable cone 317 is able to expand, as illustrated in FIG. 27D.

Figure 27G:
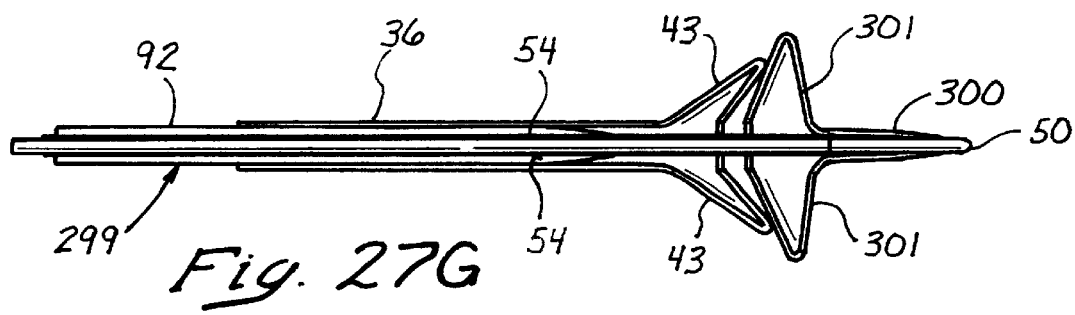
Figure 27H:
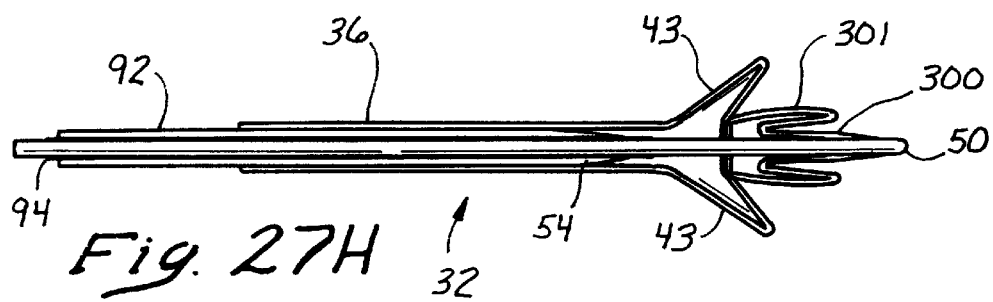
Figure 27I:
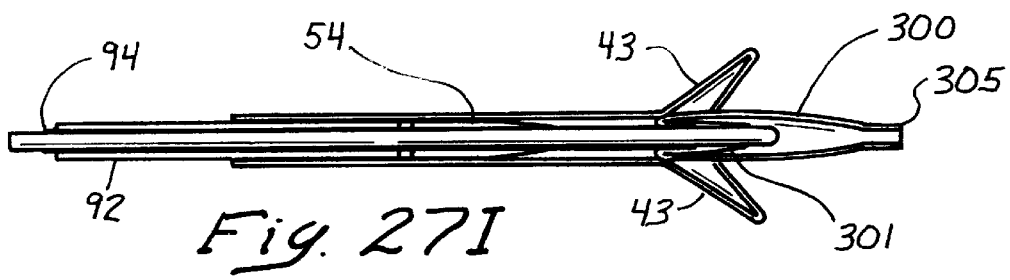
Figure 27J:
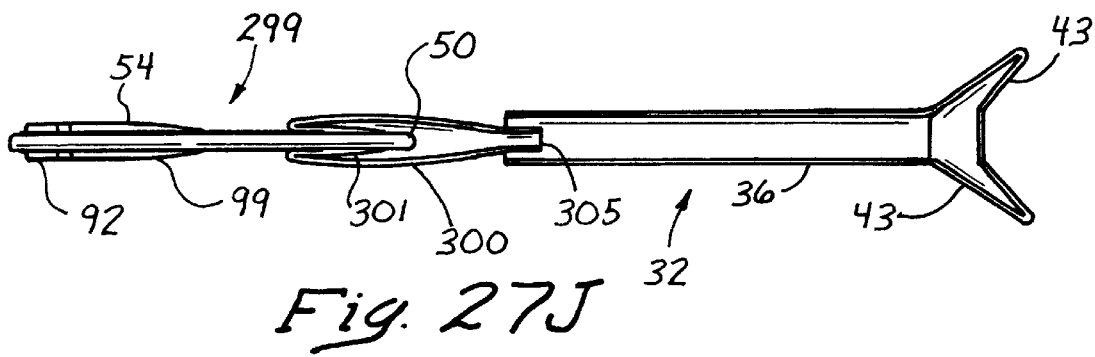
Figure 28E:
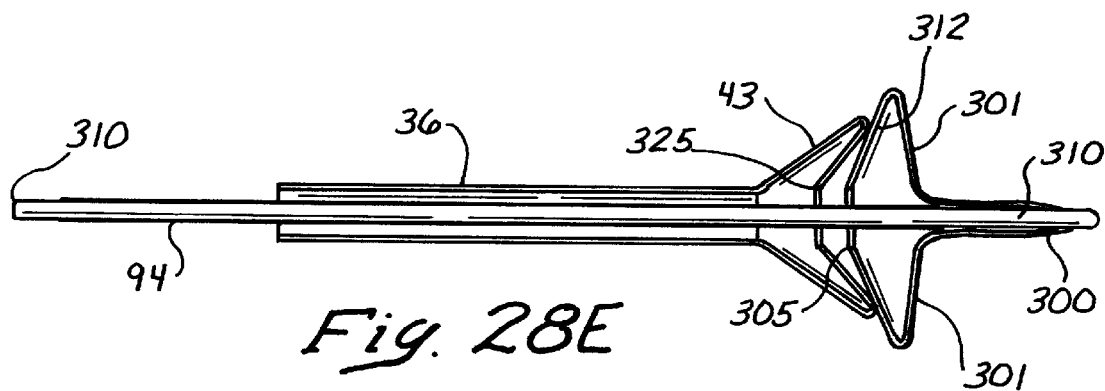
Figure 28F:
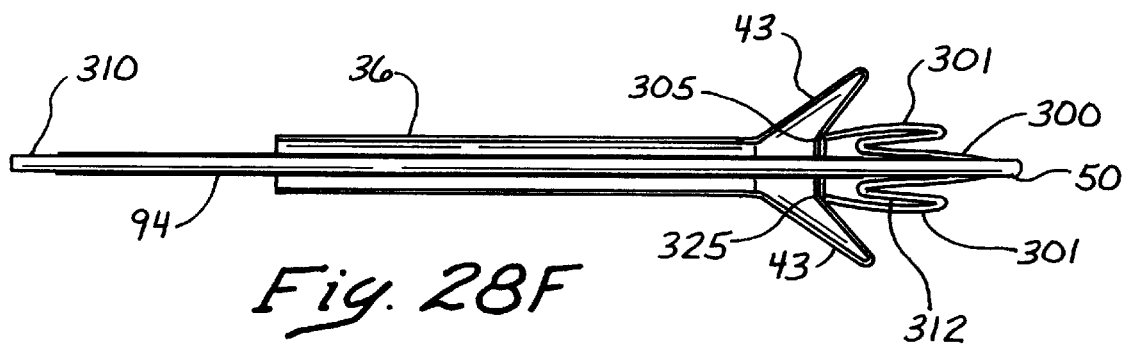
Figure 28G:
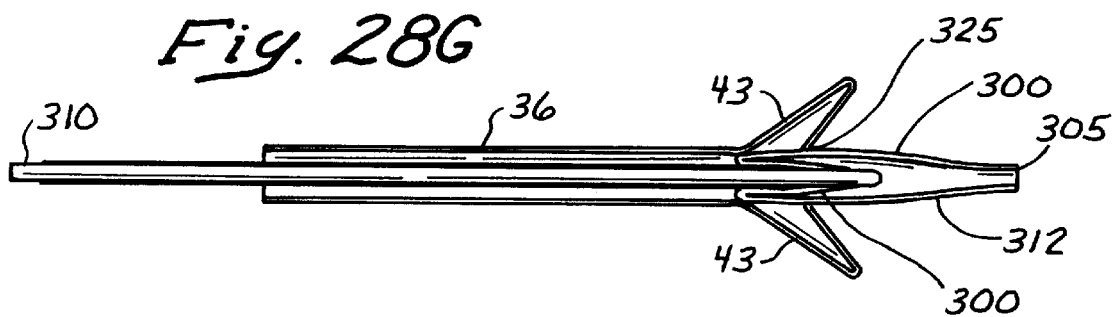
Figure 28H:
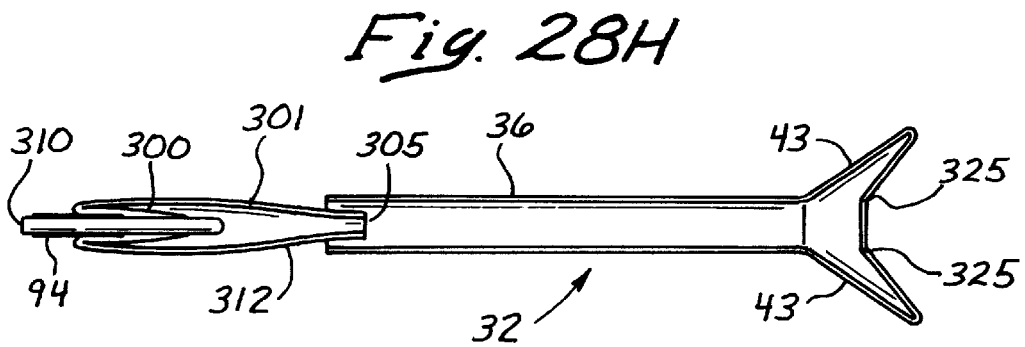

The obturator expandable cone 317 is subsequently moved proximally against the distal end 350 of the expandable containment member 333. Movement of the obturator expandable cone 317 against the distal end 350 of the expandable containment member 333 results in an expansion of the expandable containment member 333, as illustrated in FIG. 27E. After the obturator expandable cone 317 is moved into the expandable containment member 333 (FIG. 27E), the obturator expandable cone 317 is collapsed into a low-diameter configuration, as illustrated in FIG. 27F. Subsequently, the obturator expandable cone 317 is moved proximally into the expandable containment member 333 and into the outer flexible tube 321, as illustrated in FIG. 27G. Additionally, the reversible sheath 307 is moved proximally against the expandable containment member 333, as illustrated in FIG. 27G. The reversible sheath 307 is further moved proximally against the expandable containment member 333 (FIG. 27H), until the proximal sheath end 309 is moved past the distal sheath end 311, as illustrated in FIG. 27I. Movement of the proximal sheath end 309 past the distal sheath end 311 allows the reversible sheath 307 to invert and fold back onto itself as the distal end 315 is withdrawn from within the outer flexible tube 321, as illustrated in FIG. 27J.

FIGS. 28A–H illustrate a fifth alternative embodiment of the present invention, where the obturator expandable cone 317 of the fourth alternative embodiment is not used. The expandable containment member 333 is urged to a fully expanded configuration as the reversible sheath 307 is inverted and folded back onto itself during withdrawal of the distal end 315 from the outer flexible tube 321.

Although exemplary embodiments of the invention have been shown and described, many other changes, modifications and substitutions, in addition to those set forth in the above paragraph, may be made by one having ordinary skill in the art without necessarily departing from the spirit and scope of this invention.

I claim:

1. An access device for introduction into a body passage, comprising:
    an outer tube having a proximal tube end, a distal tube end, and a lumen extending between the proximal tube end and the distal tube end;
    an obturator assembly having a proximal obturator end and a distal obturator end, and being removably and concentrically disposed within the lumen of the outer tube; and
    an expandable member having a proximal member end and a distal member end, the proximal member end being connected to the distal tube end, and the distal member end being detachably connected to the distal obturator end, the expandable member being expandable by relative movement between the proximal member end and the distal member end, resulting from relative movement of the outer tube and the obturator assembly in opposite directions.

2. The access device as recited in claim 1, the outer tube being elongate and bendable to conform to a direction of a body passage.

3. The access device as recited in claim 2, the lumen of the outer tube being unobstructed, when the obturator assembly is removed therefrom, to thereby facilitate insertion and removal of instruments and material through the lumen obstruction.

4. The access device as recited in claim 3, wherein the expandable member has properties for radially compressing the obstruction material as the obstruction material moves proximally through the expandable member.

5. The access device as recited in claim 1, further comprising a guidewire, which is adapted to be inserted through the obturator assembly, the guidewire acting as a stiffener and as a leader for the access device when inserted through the obturator assembly.

6. The access device as recited in claim 1, the distal member end being adapted to be detached from the distal obturator end, when the distal member end is moved distally away from the proximal member end.

7. The access device as recited in claim 1, wherein the relative movement between the proximal member end and the distal member end comprises movement of the proximal member end and the distal member end together.

8. The access device as recited in claim 7, the expandable member being adapted to form a cone when the proximal member end and the distal member end are moved together, the cone being adapted for receiving and radially compressing an embolus or thrombus from a body passage.

9. The access device as recited in claim 8, the expandable member bending at a midpoint located on the expandable member between the proximal member end and the distal member end, when the proximal member end and the distal member end are moved together.

10. The access device as recited in claim 9, the expandable member forming a cone when the distal member end is moved proximally past the midpoint.

11. The access device as recited in claim 10, the cone being adapted for receiving an embolus or thrombus from a body passage.

12. The access device as recited in claim 1, further comprising an accessory device, which includes a port for applying a suction to the lumen of the outer tube.

13. The access device as recited in claim 12, further comprising a connector portion for connecting the outer tube to the accessory device, wherein the outer tube, the connector portion, and the expandable member together form a sheath assembly.

14. The access device of claim 1 wherein the expandable member comprises a tubular mesh.

15. An access device for introduction into a body passage, comprising:
    an outer tube having a proximal tube end, a distal tube end, and a lumen extending between the proximal tube end and the distal tube end:
    an obturator assembly having a proximal obturator end and a distal obturator end, and being removably and concentrically disposed within the lumen of the outer tube;
    an expandable member having a proximal member end and a distal member end, the proximal member end being connected to the distal tube end, and the distal member end being detachably connected to the distal obturator end, the expandable member being expandable by relative movement between the proximal member end and the distal member end, resulting from relative movement of the outer tube and the obturator assembly in opposite directions;

the distal member end being adapted to be detached from the distal obturator end when the distal member end is moved distally away from the proximal member end; and the obturator assembly comprising an obturator expandable cone, which is adapted to be expanded after the distal member end is moved distally away from the proximal member end.

16. The access device as recited in claim 15, the obturator assembly further comprising:

an intermediate slidable obturator sleeve having a proximal intermediate sleeve end, a distal intermediate sleeve end, and a lumen extending between the proximal intermediate sleeve end and the distal intermediate sleeve end;

an inner fixed obturator sleeve having a proximal inner sleeve end and a distal inner sleeve end, and being concentrically disposed within the lumen of the intermediate slidable obturator sleeve;

wherein the obturator expandable cone has a proximal cone end and a distal cone end, the distal cone end being connected to the distal inner sleeve end, and the proximal cone end being connected to the distal intermediate sleeve end, the obturator expandable cone being expandable by relative movement between the proximal cone end and the distal cone end, resulting from relative movement of the distal inner sleeve end and the distal intermediate sleeve end in opposite directions.

17. An access device, comprising:

an outer tube having a predetermined outer diameter, a lumen having a predetermined inner diameter, a proximal tube end, a distal tube end, and an axis extending between the proximal tube end and the distal tube end; and an expandable cone attached to the outer tube at the distal tube end, the expandable cone extending distally from the distal tube end and having an unexpanded diameter that is approximately equal to the predetermined outer diameter, the expandable cone being adapted for expansion by an obturator assembly removably disposed within the lumen of the flexible tube.

18. The access device as recited in claim 17, further comprising a guidewire, which is adapted to be inserted through the obturator assembly, the guidewire acting, when inserted through the obturator assembly, as a stiffener and as a leader for the access device.

19. An access device insertable into a body passage, comprising:

(a) an outer wall defining a lumen therein, the outer wall comprising:
   (1) a nonexpandable section having a predetermined diameter, a proximal end, and a distal end; and
   (2) an expandable cone attached to the distal end of the nonexpandable section, the expandable cone being expandable to an expanded diameter and being contractible to an unexpanded diameter, which is approximately equal to the predetermined diameter; and (b) an obturator assembly insertable within the lumen, the obturator assembly being adapted for expanding the expandable cone to the expanded diameter.

20. The access device according to claim 19, wherein: the obturator assembly is removable from the lumen, and a therapeutic catheter is insertable through the lumen and into the body passage, the therapeutic catheter being adapted to remove obstructing material from the body passage.

21. The access device of claim 19, wherein the expandable cone comprises a tubular mesh.

22. A tubular access device for insertion into a body passage, comprising:

a semi-rigid portion of tubing;

an expandable portion of tubing joined to the semi-rigid portion of tubing, the expandable portion of tubing having a proximal end, a distal end, and an axis extending between the proximal end and the distal end, the expandable portion of tubing being expandable in diameter by compression along the access and being reducible in diameter by stretching along the access;

the semi-rigid portion of tubing comprising a solid walled tubular member with a first diameter;

the expandable portion of tubing comprising a braided tubular component with a second diameter approximately equal to the first diameter; and the semi-rigid portion of tubing and the expandable portion of tubing being joined together by fusion.

23. The tubular access device according to claim 22, the expandable portion of tubing being coated with a non-permeable elastomeric material, which forms a barrier to flow within the body passage when the expandable portion of tubing is expanded.

24. A tubular access device for insertion into a body passage, comprising:

an outer tube having a proximal tube end and a distal tube end;

an obturator tube disposed within the outer tube, the obturator tube having a proximal obturator end and a distal obturator end;

an expandable member connected to both the distal tube end and the distal obturator end; and a guidewire removably disposed within the obturator tube, the guidewire being adapted for adding support to the outer tube and the obturator tube when the tubular access device is inserted into the body passage.

25. The tubular access device of claim 24 wherein the expandable member comprises a tubular mesh.

26. A tubular access device for removing obstructing material from a body passage, comprising:

an expandable member having a first diameter in a low-profile state and a second diameter larger than the first diameter in a high-profile state;

two coaxial members, each coaxial member having a distal end that is connected to the expandable member; and the expandable member in the high-profile state having the shape of a funnel with a distally-facing surface extending radially outwardly with progressive distal positions.

27. A method of removing an obstructing material from a body passage, comprising the following steps:

inserting a tubular access device into the body passage, the tubular access device having an expandable containment member with a proximal end and a distal end;

moving the tubular access device in a distal direction within the body passage to a first location where obstructing material is located within the body passage;

moving the distal end of the expandable containment member toward the proximal end of the expandable containment member, to thereby expand the expandable containment member into the shape of a cone;

advancing a therapeutic catheter in the distal direction past the first location where the obstructing material is located to a second location;

retracting the therapeutic catheter in a proximal direction from the second location toward the expandable containment member, to thereby move the obstructing material into the expandable containment member; and during the retracting step, radially compressing the obstructing material by moving the obstructing material progressively through the cone.

28. The method of removing an obstructing material from a body passage according to claim 27, wherein the step of moving the distal end of the expandable containment member toward the proximal end of the expandable containment member comprises the following steps:

providing an obturator in contact with the distal end of the expandable containment member; and moving the obturator in the proximal direction, to thereby move the distal end of the expandable containment member toward the proximal end of the expandable containment member.

29. The method of removing an obstructing material from a body passage according to claim 28, further comprising a step of removing the obturator from the tubular access device.

30. The method of removing an obstructing material from a body passage according to claim 29, further comprising the step of operating the expandable containment member as a therapeutic catheter after the obturator is removed from the tubular access device.

31. The method of removing an obstructing material from a body passage according to claim 28, further comprising the following substeps:

removing the obturator from the tubular access device to expand the containment member into the shape of a funnel;

inserting a therapeutic catheter into the tubular access device;

advancing the therapeutic catheter in a distal direction past the obstructing material; and retrieving the therapeutic catheter in a proximal direction to thereby draw the obstructing material into the funnel of the expanded containment member.

32. The method of claim 27 wherein the second moving step includes the step of providing a containment member in the form of a tubular mesh.

33. A tubular access device, comprising:

a tube having a proximal tube end, a distal tube end, and an axis extending from the proximal tube end to the distal tube end; and a changeable member having a proximal member end, an intermediate member area, and a distal member end, the changeable member being connected to the distal tube end and being adapted to be changed from a tubular configuration into a funnel-shaped configuration by inverting the distal member end into the intermediate member area.

34. The tubular access device as recited in claim 33, the changeable member being adapted to be changed from a tubular configuration into a funnel-shaped configuration when the distal member end is moved into close proximity with the proximal member end.

35. The tubular access device of claim 33, wherein the changeable member includes a tubular mesh.

* * * * *